(12) United States Patent
Bluchel et al.

(10) Patent No.: US 9,138,524 B2
(45) Date of Patent: Sep. 22, 2015

(54) SENSING SYSTEM FOR DETECTING A SUBSTANCE IN A DIALYSATE

(71) Applicant: Temasek Polytechnic, Singapore (SG)

(72) Inventors: Christian Gert Bluchel, Singapore (SG); Yanmei Wang, Singapore (SG); Hua Zhang, Singapore (SG); Jui Pin Er, Singapore (SG); Kim Jyh Wong, Singapore (SG)

(73) Assignee: Temasek Polytechnic, Singapore (SG)

( * ) Notice: Subject to any disclaimer, the term of this patent is extended or adjusted under 35 U.S.C. 154(b) by 0 days.

(21) Appl. No.: 14/352,283

(22) PCT Filed: Nov. 8, 2012

(86) PCT No.: PCT/SG2012/000425
§ 371 (c)(1),
(2) Date: Apr. 16, 2014

(87) PCT Pub. No.: WO2013/070172
PCT Pub. Date: May 16, 2013

(65) Prior Publication Data
US 2014/0291218 A1  Oct. 2, 2014

(30) Foreign Application Priority Data

Nov. 8, 2011 (SG) ................ PCT/SG2011/000395

(51) Int. Cl.
*A61M 1/16* (2006.01)
*A61M 1/28* (2006.01)
(Continued)

(52) U.S. Cl.
CPC ............... *A61M 1/28* (2013.01); *A61M 1/1609* (2014.02); *A61M 1/1696* (2013.01); *B01D 61/30* (2013.01); *G01N 33/0021* (2013.01); *G01N 33/0054* (2013.01); *G01N 2001/1454* (2013.01)

(58) Field of Classification Search
CPC ....... A61M 1/16; A61M 1/28; A61M 1/1619; A61M 1/1609; A61M 1/1694; B01D 61/24; B01D 61/243; B01D 61/30; G01N 33/0021; G01N 33/0054; G01N 33/009; G01N 33/0009; G01N 33/0011; G01N 33/0013; G01N 33/0019; G01N 1/20; G01N 1/2205; G01N 33/00; G01N 2001/1445; G01N 2001/1454; G01N 2001/2007; B01L 5/00; B01L 15/00; B01L 2400/0475
USPC ........................ 210/85, 96.2, 120, 321.6, 646; 604/5.01, 6.01, 6.09, 29, 65; 73/31.05, 73/863.23; 436/113; 204/415, 431, 432
See application file for complete search history.

(56) References Cited

U.S. PATENT DOCUMENTS 3,545,931 A * 12/1970 McKinley, Jr. ................ 436/113
5,008,078 A *  4/1991 Yaginuma et al. ............ 422/422
(Continued)

FOREIGN PATENT DOCUMENTS

WO   WO 2007/082565 A1   7/2007
WO   WO 2009/157878 A1   12/2009

*Primary Examiner* — Joseph Drodge
(74) *Attorney, Agent, or Firm* — Brinks Gilson & Lione; Eric D. Babych

(57) ABSTRACT

A sensing system for detecting a substance in a dialysate. The system includes a hydrophobic barrier capable of allowing the substance in the dialysate to equilibrate to a gas; a detector capable of detecting the gas; an interface disposed between the hydrophobic barrier and the detector and configured to allow fluid communication of the gas; and one or more delivery mechanisms capable of transporting the gas from the hydrophobic barrier to the detector. A method of detecting ammonium gas in a dialysate is also provided.

19 Claims, 38 Drawing Sheets

(51) Int. Cl.
  *B01D 61/30* (2006.01)
  *G01N 33/00* (2006.01)
  *G01N 1/14* (2006.01)

(56) References Cited

U.S. PATENT DOCUMENTS

| | | | |
|---|---|---|---|
| 5,882,937 A * | 3/1999 | Sauer et al. | 436/113 |
| 6,541,272 B1 * | 4/2003 | Mitra | 436/178 |
| 7,949,477 B2 * | 5/2011 | Rinne et al. | 702/23 |
| 8,715,254 B2 * | 5/2014 | Nishtala | 604/318 |
| 2003/0113931 A1 | 6/2003 | Pan et al. | |
| 2003/0113932 A1 * | 6/2003 | Sternberg et al. | 436/113 |
| 2005/0150832 A1 | 7/2005 | Tsukamoto | |
| 2007/0161113 A1 | 7/2007 | Ash | |
| 2007/0179431 A1 | 8/2007 | Roberts et al. | |
| 2009/0078862 A1 * | 3/2009 | Rodier et al. | 250/282 |
| 2010/0312174 A1 | 12/2010 | Hoffman | |
| 2011/0213230 A1 * | 9/2011 | Lindgren et al. | 600/365 |

* cited by examiner

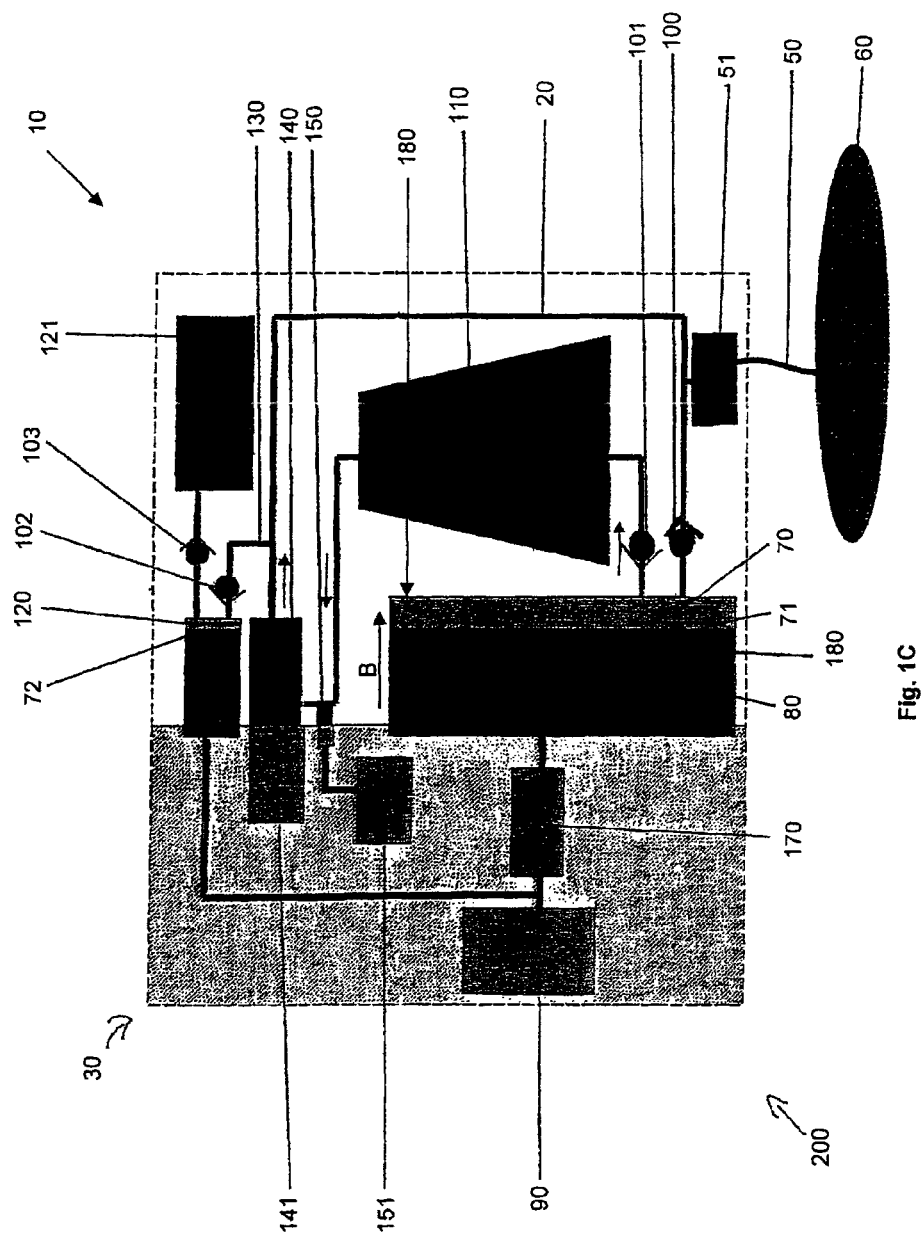

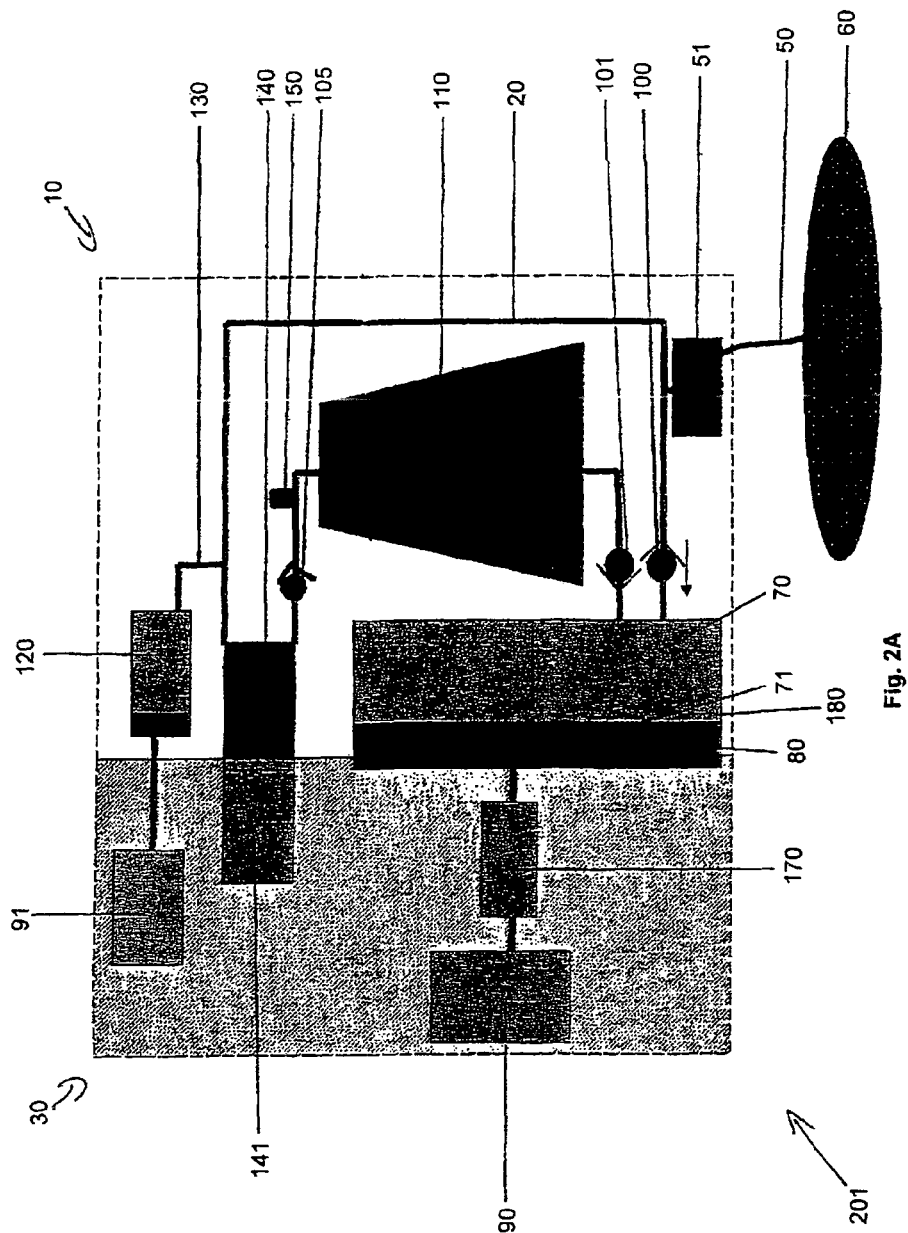

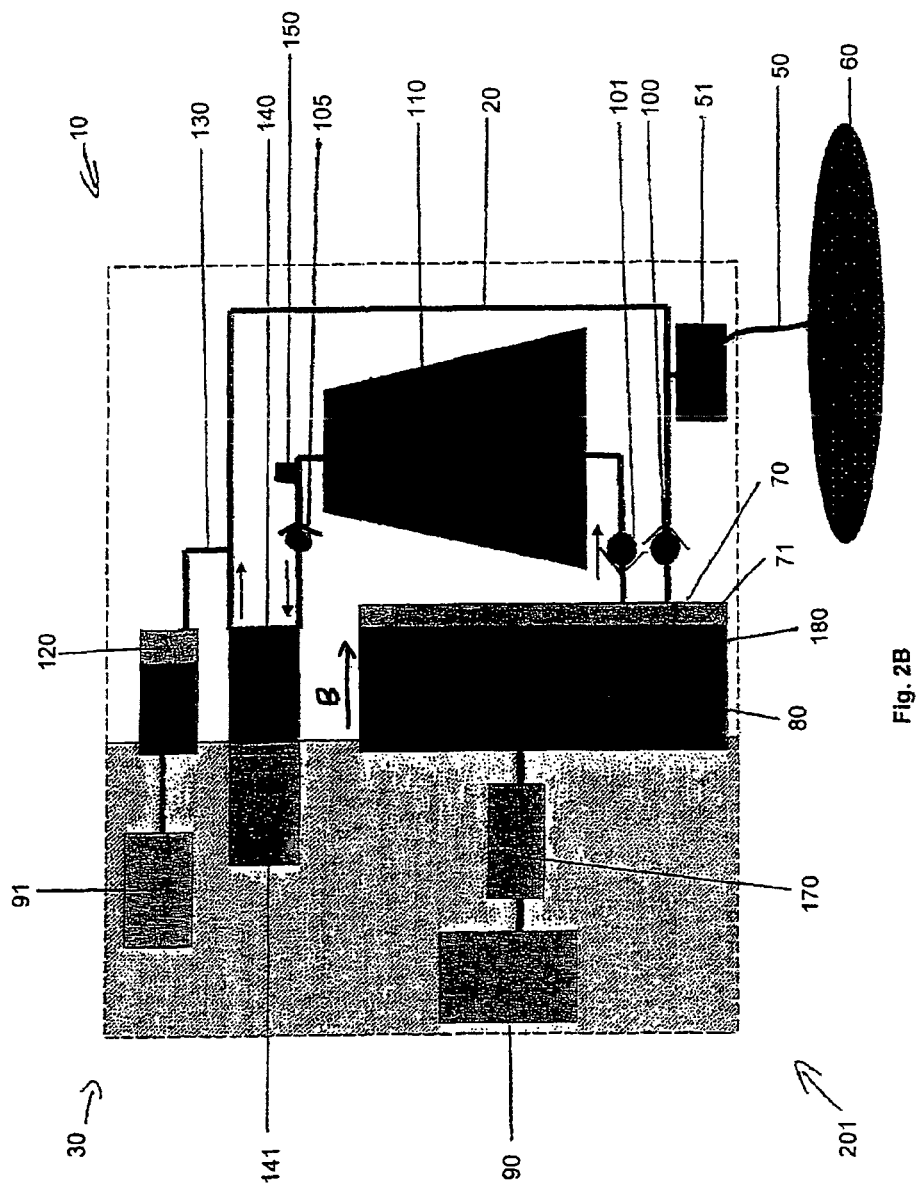

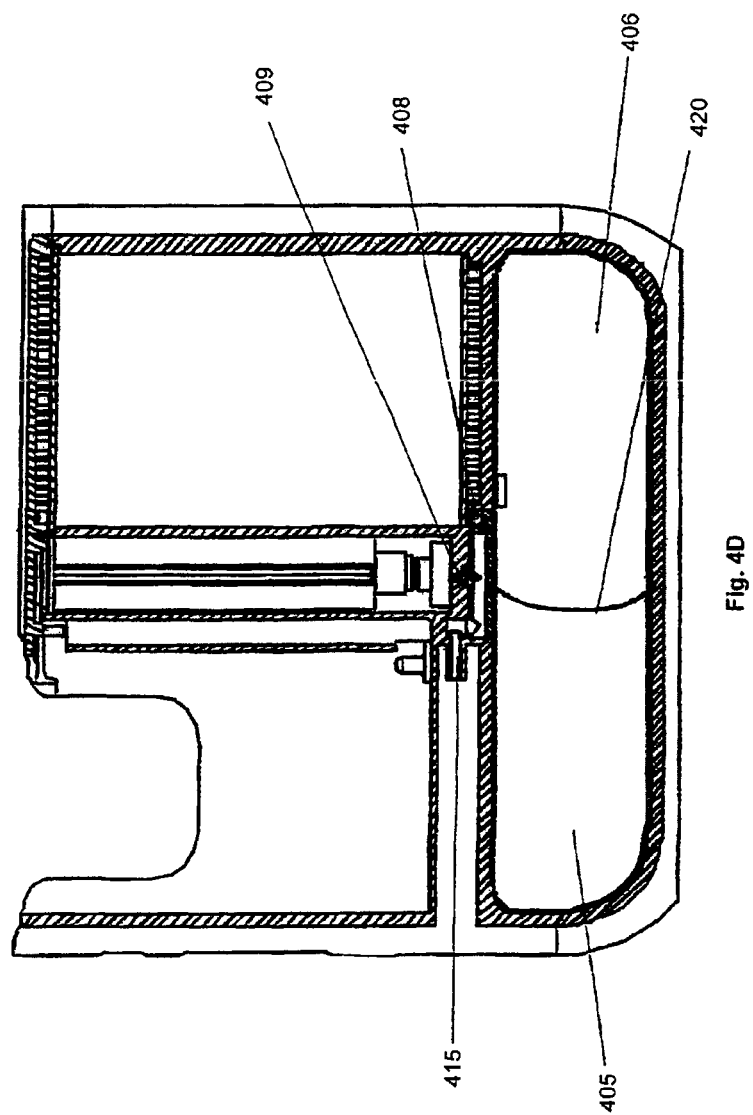

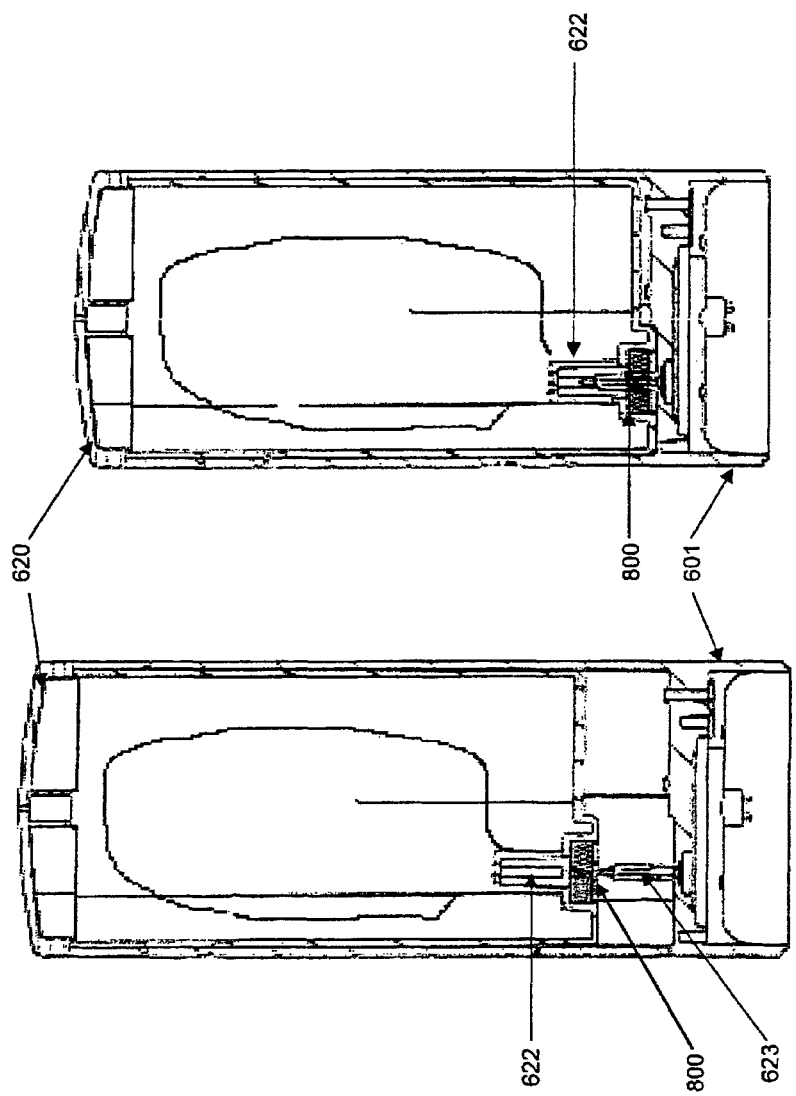

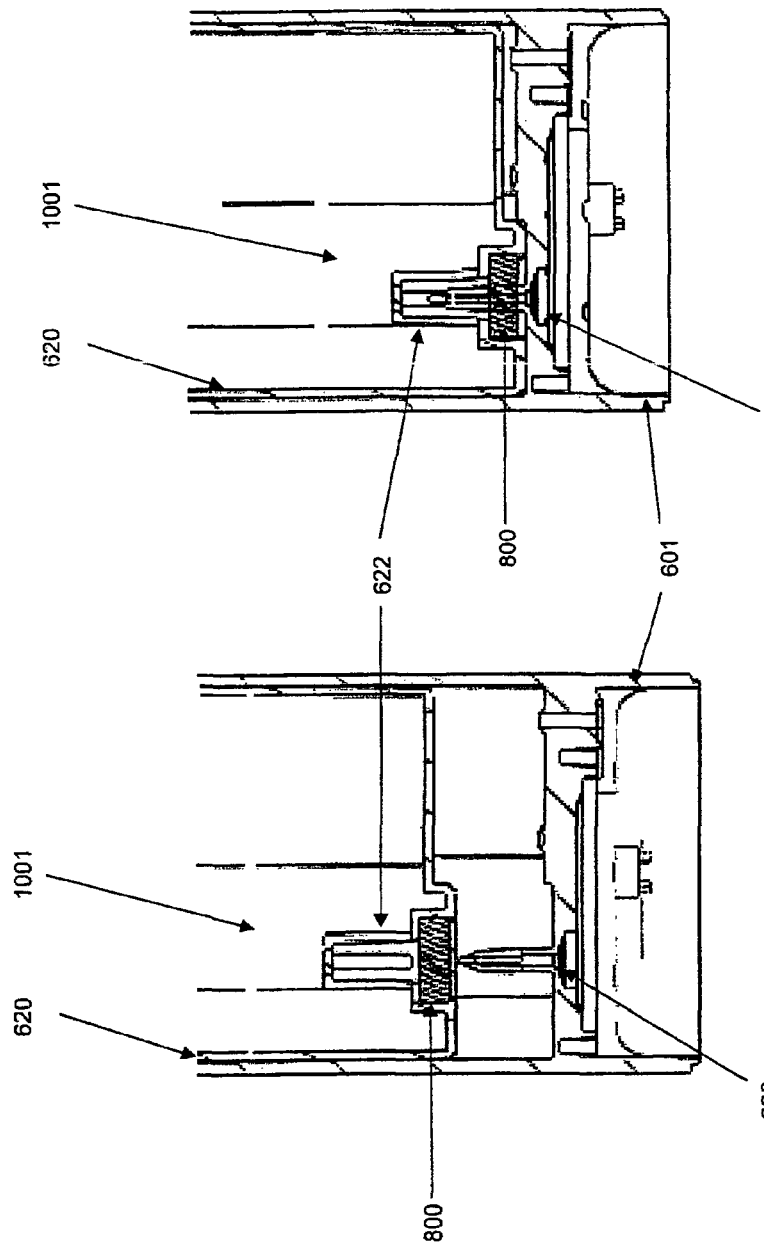

SENSING SYSTEM FOR DETECTING A SUBSTANCE IN A DIALYSATE

CROSS-REFERENCE TO RELATED APPLICATIONS

The present application is a U.S. National Phase §371 application of International Application No. PCT/SG2012/000425, filed Nov. 8, 2012, and PCT/SG2011/000395, filed Nov. 8, 2011, which in turn claims priority from U.S. Provisional Patent Application No. 61/549,968, filed Oct. 21, 2011, all of which applications are incorporated herein by reference in their entirety.

TECHNICAL FIELD

The present invention relates to a dialysis device and in particular to a portable or wearable dialysis device. The invention also relates to a method of conducting dialysis. The invention also relates to a sensing system for detecting ammonium in a dialysate.

BACKGROUND

Kidneys are vital organs of the human homeostasis system. Kidneys act as a natural filter in the body which remove toxic metabolic wastes such as urea from the blood. Kidney failure or malfunction may lead to an accumulation of toxins and to an imbalanced electrolyte level in the blood, which may result in undesirable repercussions that are hazardous to an individual's health.

Renal dysfunction and/or failure and, in particular, end-stage renal disease, may cause the body to lose the ability to adequately remove toxic waste in the blood and restore the optimal level of electrolytes in the blood, within physiological ranges. Dialysis is commonly used to replace inadequate kidney function by removing toxic waste.

For the past few years, the predominant form of dialysis used for patients with end-stage renal disease (ESRD) is hemodialysis. Hemodialysis involves the use of an extracorporeal system for the removal of toxins directly from the patient's blood by passing a large amount of the patient's blood through a filtering unit or dialyzer. Hemodialysis treatment typically lasts several hours and must be performed under medical supervision three to four times a week, which significantly decrease a patient's mobility and quality of life. Furthermore, as hemodialysis is performed periodically rather than on a continuous basis, patient health deteriorates as soon as a "treatment cycle" in which contaminants are removed has been completed.

The other form of dialysis used for patients with kidney failure is peritoneal dialysis, most commonly applied in the following two techniques: "continuous ambulatory peritoneal dialysis" (CAPD) and "automated peritoneal dialysis" (APD). In CAPD, fresh dialysate is infused into the patient's abdominal (peritoneal) cavity where, by means of diffusion, metabolic waste and electrolytes in the blood are exchanged with the dialysate across the peritoneal membrane. To allow sufficient diffusion of the electrolytes and metabolic waste to occur, the dialysate is retained in the abdominal (peritoneal) cavity for a couple of hours before removal and replacement (of the spent dialysate) with fresh dialysate. Major drawbacks of continuous ambulatory peritoneal dialysis are a low level of toxin clearance, and the need to continuously replace the spent dialysate, which can be arduous for the patient and disruptive to his/her daily activities.

To address this problem, devices have been designed that reconstitute used/spent dialysate from hemodialysis and/or peritoneal dialysis as opposed to discarding it. However, current devices that reconstitute used/spent dialysate have several associated disadvantages including complex set up procedures and difficulties in maintaining the sterility of components. A further disadvantage is that current devices often require a plurality of fluid connections, which increases the risk of introducing biological contamination and reduces sterility of the device. In addition several components must be disposed of either daily, weekly or monthly adding another layer of complexity to the operation of such devices. In addition, the flow system of known regenerating dialysis devices requires a plurality of pumps, which in turn undesirably increases the overall size, weight and power consumption of the device.

Accordingly, there is a need to provide a dialysis device that overcomes or at least ameliorates one or more of the disadvantages described above. There is also a need to provide a dialysis device without compromising on the size, weight and power consumption of the device.

Furthermore, an ideal artificial kidney should simulate a normal kidney by providing continuous metabolic and fluid control, removal of toxins, and unrestricted patient freedom. As mentioned above, hemodialysis, continuous ambulatory peritoneal dialysis (CAPD), automated peritoneal dialysis (APD) and "24/7" wearable, peritoneal-based artificial kidneys (WAK) are some methods that help renal failure patients to remove metabolic waste. Some of these methods, e.g. the "24/7" wearable, peritoneal-based artificial kidneys (WAK), provide optimal clearance of uremic toxins by continuously regenerating the dialysate using sorbent cartridge technology.

Methods utilizing sorbent cartridge technology typically require a safety mechanism to monitor the exhaustion of the sorbent. Before or when the sorbent is exhausted or does not function well, users need to replace the cartridge to prevent returning toxins back to the patient. One common approach is to monitor the ammonium concentration of the regenerated dialysate to check that it is under a safe level.

However, there are difficulties in dialysis ammonia/ammonium detection. A known method of monitoring the regenerated peritoneal dialysate ammonium concentration in-line is to incorporate an ammonia/ammonium sensor directly onto the dialysate liquid line. In other words, the sensing system is part of the dialysate flow. However, this method requires the ammonia/ammonium sensing system to maintain its sterility at all times, as well as function well. Also, there may be biocompatibility issues. Further, the sensing system has to be compatible with liquid phase applications.

Currently, many liquid phase applications of sensing and monitoring ammonia/ammonium level have their drawbacks and limitations. As such, they are unsuitable for use in peritoneal dialysis.

Besides directly incorporating an ammonia/ammonium sensor in the regenerated dialysate liquid line, it is possible to incorporate a sensor beside the liquid dialysate to monitor the ammonium concentration. For example, US 2007/0161113 A1 and WO 2007/082565 A2 disclose an optical ammonia detecting device where an ammonia sensitive material is placed directly adjacent to a liquid flow path containing regenerated dialysate. The components for the optical detection device are placed adjacent to the ammonia sensitive material, together with the electrical accessories for data processing and signal detection.

However, due to the close proximity of the ammonia sensing material to the hydrophobic membrane, the electrical accessories are disposed very close to the dialysate line. This approach also requires a closed "opaque casing" to prevent any external light interference, which increases manufacturing complexity. Electrical accessories for data processing and signal detection are relatively bulky. Accordingly, miniaturization of portable and wearable peritoneal dialysis devices is difficult. Additional drawbacks of this concept may also include:

Disposable/single use for the ammonia sensing material/part;

Need for patients to assemble the cartridge for use;

Very close/or direct contacting sensor causes potential dialysate leaching leading to a biocompatibility concern Possible improper assembly may cause inaccuracy Detection methods and systems disclosed in other publications have several drawbacks such as non-biocompatibility, assembly difficulties (e.g. improper assembly may cause inaccuracies), bulkiness, single-use ammonia sensing components and sterility concerns.

Accordingly, there is also a need to provide a sensing system for detecting ammonium in a dialysate that overcomes or at least ameliorates one or more of the disadvantages described above.

SUMMARY

Definitions

The following words and terms used herein shall have the meaning indicated:

The term "sorbent" as used herein broadly refers to a class of materials characterized by their ability to adsorb and/or absorb the desired matter of interest.

The term "non-toxic" as used herein refers to a substance that causes little to no adverse reactions when present in the human body.

The term "contaminants" in the context of this specification, means any constituents, typically toxic constituents, within a dialysate that are generally harmful to human health and which are desirable to be removed in a dialysate detoxification process. Typical contaminants include, but are not limited to ammonium, phosphates, urea, creatinine and uric acid.

The term "biocompatible" as used herein refers to the property of a material that does not cause adverse biological reactions to the human or animal body.

The term "upstream" as used herein refers to a localization within the flow path, relative to a point of reference, and in direction opposite to that of the dialysate flow. The term "downstream" as used herein refers to a localization within the flow path, relative to a point of reference, and in direction of the dialysate flow.

The term "crack-pressure" as used herein refers to the point at which the internal pressure of a pneumatic system triggers the opening of a valve.

The term "regenerate" as used herein refers to the action of detoxifying dialysate by removal of uremic toxins.

The term "reconstitute" as used herein refers to the action of converting regenerated dialysate to essentially the same state and chemical composition as fresh peritoneal dialysate prior to dialysis.

The term "outflow mode" as used herein refers to the flow of dialysate from the patient's body through a sorbent. The flow is referenced from the patient's body.

The term "inflow mode" as used herein refers to the flow of the dialysate from a sorbent to the patient's body. The flow is referenced to the patient's body.

The term "fluid" as used herein refers to a liquid or a gas.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DISCLOSURE OF OPTIONAL EMBODIMENTS

One aspect of the present invention provides a sensing system for detecting a substance in a dialysate The sensing system may include a hydrophobic barrier capable of allowing the substance in the dialysate to equilibrate to a gas; a detector capable of detecting the gas; an interface disposed between the hydrophobic barrier and the detector and configured to allow fluid communication of the gas; and one or more delivery mechanisms capable of transporting the gas from the hydrophobic barrier to the detector.

In one embodiment, the one or more delivery mechanisms provides a driving force capable of transporting the gas from the hydrophobic barrier to the detector.

In one embodiment, the driving force circulates the gas within the interface. In a further embodiment, the driving force moves the gas back and forth within the interface.

In one embodiment, the sensing system may further include electronic control means configured to control the driving force.

In one embodiment, the one or more delivery mechanisms may include a carrier gas.

In one embodiment, the interface is about 1 cm to 50 cm in length.

In one embodiment, the substance is ammonium and the gas is ammonia gas.

In one embodiment, the hydrophobic barrier may be capable of separating the ammonium in the dialysate from the ammonia gas in the interface.

In one embodiment, the substance is a volatile organic compound used for the detection of medical conditions.

In one embodiment, the hydrophobic barrier may be a degasser barrier.

In one embodiment, the hydrophobic barrier may be a bacteria filter.

In one embodiment, the hydrophobic barrier may be a functional part of a dialysis device.

In one embodiment, the interface may include one or more ammonia gas compatible materials.

In one embodiment, the interface may be a non-porous material.

In one embodiment, the interface may include condensation reduction means within the interface.

In one embodiment, the system may further include an electronic processor electrically connected to the detector, the electronic processor configured to obtain readings from the detector, process the readings and/or trigger an alarm when the readings exceed a predetermined threshold.

In one embodiment, the system may be configured to use an ammonia gradient to detect exhaustion.

An alternate aspect of the present invention provides a dialysis device that includes the sensing system as described above.

In one embodiment, the dialysis device may be a peritoneal dialysis device.

In one embodiment, the dialysis device may be a hemodialysis device.

An alternate aspect of the present invention provides a method of detecting ammonium in a dialysate. The method may include the steps of providing a hydrophobic barrier capable of allowing ammonium in the dialysate to equilibrate to ammonia gas; providing a detector capable of detecting ammonia gas; disposing a channel between the hydrophobic barrier and the detector, and configuring the channel to allow fluid communication of the ammonia gas; and providing one or more delivery mechanisms capable of transporting the ammonia gas from the hydrophobic barrier to the detector.

BRIEF DESCRIPTION OF DRAWINGS

The accompanying drawings illustrate a disclosed embodiment and serve to explain the principles of the disclosed embodiment. It is to be understood, however, that the drawings are designed for purposes of illustration only, and not as a definition of the limits of the invention.

FIG. 1c is a schematic diagram of one embodiment of the disclosed dialysis device, wherein the flow of the dialysate is from the storage chamber to the peritoneal cavity.

FIG. 2a is a schematic diagram of an alternative embodiment of the disclosed dialysis device, wherein the flow of the dialysate is toward the storage chamber from the peritoneal cavity.

FIG. 2b is a schematic diagram of the embodiment of FIG. 2a, wherein the flow of the dialysate is from the storage chamber toward the peritoneal cavity.

FIGS. 4a-d are a cross sectional views of a prototype of a disposable housing in accordance with an embodiment of the present disclosure.

FIG. 9 is a cross sectional view of a sealed connector of the additive dispensing means in accordance with the disclosure.

FIG. 10 is a cross sectional view of an embodiment of an additive dispensing means in accordance with the disclosure.

FIGS. 22a and 22b illustrate the dialysate in-flow and dialysate out-flow phases of the embodiment of the ammonia sensing system shown in FIG. 21a.

FIG. 23 shows one example of a timing diagram for a control method implemented for the embodiment of the ammonia sensing system shown in FIG. 21a.

In the figures, like numerals denote like parts.

DETAILED DESCRIPTION OF THE EMBODIMENTS

Figure 1A:
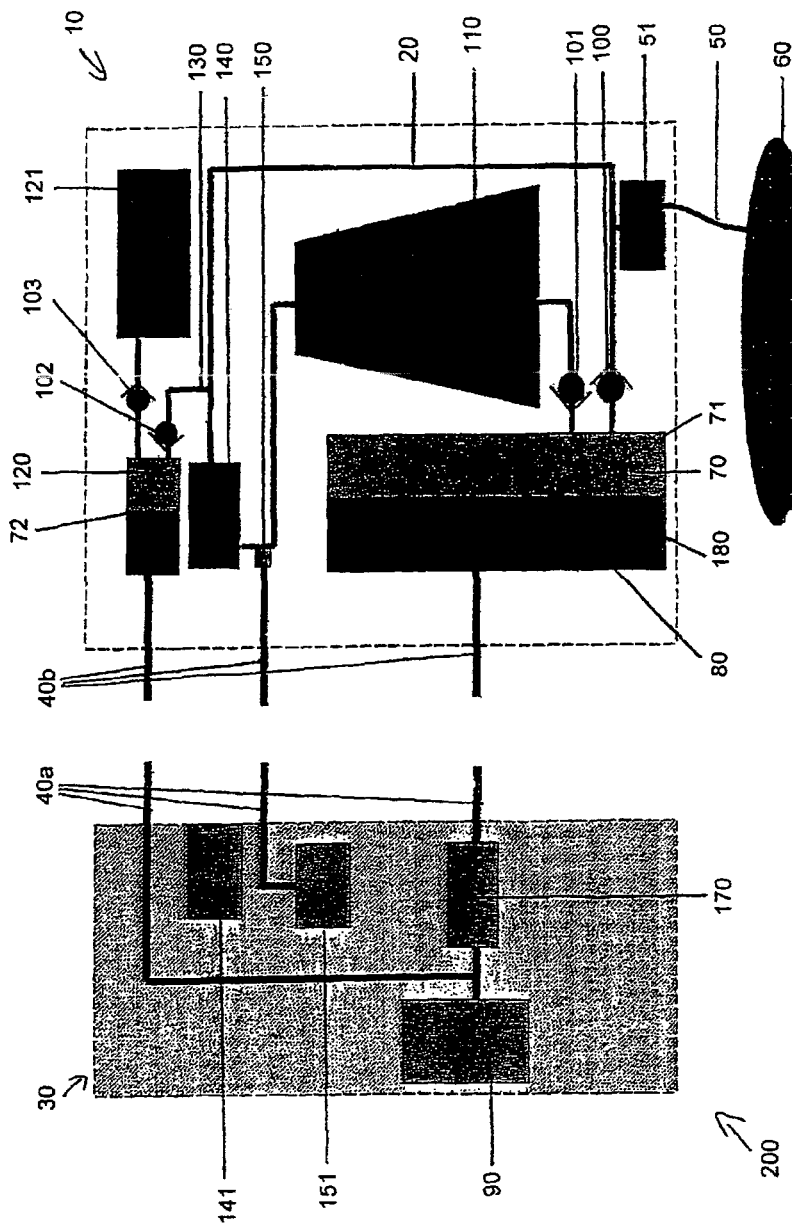
FIG. 1a is a schematic diagram of one embodiment of the disclosed dialysis device.

Referring to FIG. 1a, there is shown one embodiment of the disclosed dialysis device (200).

The dialysis device comprises a disposable housing (10) having a flow path in the form of conduit (20), a controller in the form of a control housing (30) for controlling the operation of the disposable housing (10). In this figure the disposable housing (10) and control housing (30) are not operably connected to each other. The disposable housing (10) and control housing (30) comprise interface means in the form of a conduit connector (40a) disposed on said control housing (30) and (40b) disposed on the disposable housing (10) capable of connecting the control housing and the disposable housing. The disposable housing (10) and control housing (30) are brought into operative engagement when the conduit connector (40a) is brought into locking engagement with conduit connector (40b) The conduit (20) of the disposable housing (10) is fluidly sealed from the control housing (30) and conduit connector (40a,40b).

The dialysis device comprises a flexible dialysate tube (50) which is capable of being in fluid communication with the peritoneal cavity (60) and a conduit (20). The dialysis device further comprises a storage chamber (70) located in a rigid compartment (180). The storage chamber (70) comprises a deformable diaphragm (71) integrally formed in one of the walls of the storage chamber (70). The deformable diaphragm (71) is in fluid communication on one side with the dialysate conduit (20) and, on another opposite side, in fluid communication with a pressure chamber (80). When the disposable housing (10) and control housing (30) are operably coupled to each other, the conduit connector (40a,40b) fluidly couples the pressure chamber (80) of the disposable housing (10) to a pump (90) located in the control housing (30).

The pump (90) is configured to actuate the deformable diaphragm (71), by inducing a pressure change in the pressure chamber (80) which deforms the deformable diaphragm (71) and thereby moves dialysate within said dialysate conduit (20).

Check valves (100,101,102,103) are disposed along the conduit (20) and are configured to, in the outflow mode, allow the dialysate to flow from the peritoneal cavity (60) to the storage chamber (70), and in the inflow mode allow the dialysate to flow from the storage chamber (70) to said sorbent zone (110) for removal of contaminants therein, and further permit the dialysate substantially free of said contaminants to flow back to the peritoneal cavity (60).

The disposable housing is also provided with an enrichment module (120), for dispensing a preselected amount of an enrichment solution into the dialysate, in fluid communication with the conduit (20) via a conduit (130). The enrichment module is also in fluid communication with an enrichment solution reservoir (121). The pump (90) is in fluid communication with a deformable membrane (72) of the enrichment module 120 via conduit connector (40a,40b), when the disposable housing (10) and control housing (30) are in operable engagement.

An ammonia sensor (140) is also provided downstream of the sorbent zone (110) to detect any ammonia in the dialysate. Ammonia is detected by the ammonia detector (141) when the disposable housing (10) and control housing (30) are operably coupled to each other.

A degasser in the form of a hydrophobic membrane (150) is also located downstream of the sorbent zone. The external side of the hydrophobic membrane (150) is in fluid communication with a vacuum pump (151) via the conduit connector (40a, 40b) when the control housing and disposable housing are operably coupled.

Figure 1B:
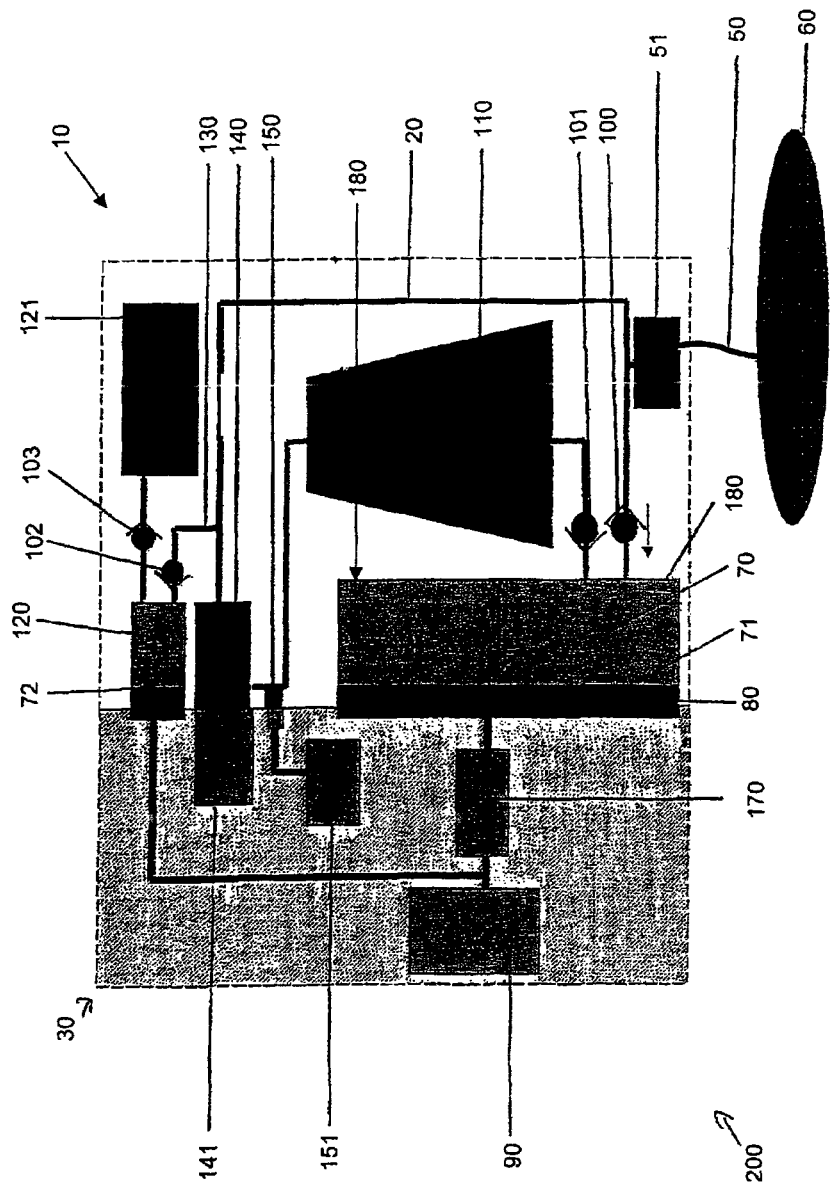
FIG. 1b is a schematic diagram of one embodiment of the disclosed dialysis device, wherein the flow of the dialysate is toward the storage chamber from the peritoneal cavity.

Referring now to FIG. 1b, there is the embodiment of FIG. 1a showing the disposable housing (10) and control housing (30) operably coupled with each other, operating in an outflow mode, wherein the flow of the dialysate is toward the storage chamber (70) from the peritoneal cavity (60) of a patient. The pump (90) actuates the deformable diaphragm (71), by inducing negative pressure in the pressure chamber (80). The negative pressure in the pressure chamber (80) deforms the deformable diaphragm (71) by biasing the deformable diaphragm (71) in the direction of arrow A and thereby moves dialysate from said peritoneal cavity (60) of the patient into the dialysate conduit (20) via bubble trap (51). The dialysate flows to the storage chamber (70) through check valve (100). A pressure sensor (170) is located in operable communication with the pump (90) to establish a preselected negative pressure within the pressure chamber (80) and to determine if the pressure of the dialysate being withdrawn from the peritoneal cavity (60) is within a safe limit.

The pump (90) operates intermittently under the control of the pressure sensor (170) to maintain the negative pressure in the pressure chamber (80) within a preselected range. Once the storage chamber (70) is full of dialysate, this is detected by the pressure sensor (170), triggering the inversion of the pump direction and thus converting the system to an inflow mode.

The pump 90 is also in fluid communication with a diaphragm (72) integrally formed in a wall of said enrichment module (120). At the same time as the storage chamber (70) is actuated under negative pressure, the enrichment module (120) is also actuated under negative pressure by the pump (90), such that a predetermined amount of an enrichment solution is withdrawn from an enrichment solution reservoir (121) though check valve (103) into the enrichment module (120). Check valve (102) ensures that no dialysate is withdrawn into the enrichment module (120) from the conduit (20).

Referring to FIG. 1c, the flow system of FIG. 1b is shown in the inflow mode, wherein the flow of the dialysate is from the storage chamber (70) to the peritoneal cavity (60). Once the storage chamber (70) is full, the pump (90) actuates the deformable diaphragm (71), by inducing positive pressure in the pressure chamber (80).

The positive pressure in the pressure chamber (80) deforms the deformable diaphragm (71) by biasing the deformable diaphragm (71) in the direction of arrow B and thereby moves dialysate from the storage chamber (70) and check valve (100) closes preventing dialysate from returning to the peritoneal cavity (60) before being treated to remove contaminants.

The pressure sensor (170) monitors the pressure in the pressure chamber (80) to ensure that the pressure of the dialysate being returned to the peritoneal cavity (60) in the inflow mode is within a safe limit.

The dialysate flows from the storage chamber (70) into the sorbent zone (110) through check valve (101). The regenerated dialysate from the sorbent zone (110) then flows past a degasser in the form of a hydrophobic membrane (150). The external side of the membrane is subjected to negative pressure by a vacuum pump (151) to aid the removal of gas generated during the dialysis procedure. The dialysate then flows through an ammonia sensor (140) which monitors the level of ammonia in the regenerated dialysate, to ensure that the ammonia level does not exceed a safe limit, prior to returning to the peritoneal cavity (60) of a patient. Ammonia is detected by the ammonia detector (141).

The regenerated dialysate then flows past an enrichment module (120). In the inflow mode, the pump (90) actuates the diaphragm (72) of the enrichment module (120), which has previously been primed with a volume of enrichment solution from the enrichment solution reservoir (121), under positive pressure. As the enrichment module (120) is actuated, check valve (103) closes to ensure that the enrichment solution does not flow back into the enrichment solution reservoir (121). The enrichment module (120) then dispenses a preselected amount of enrichment solution containing desired substances, such as electrolytes, osmotic agents, nutrients, medication and the like, into the dialysate conduit (20) through check valve (102) and conduit (130).

The regenerated dialysate then flows back to the peritoneal cavity (60) through the bubble trap (51) and flexible dialysate conduit (50).

As in the outflow mode, the pump (90) is operated intermittently under the control of the pressure sensor (170) to maintain the positive pressure in the pressure chamber (80) within a preselected range. Once the storage chamber is empty of dialysate, the pressure sensor (170) detects this and inverts the pump direction and converts the system to the outflow mode to repeat the dialysis cycle.

Figure 1D:
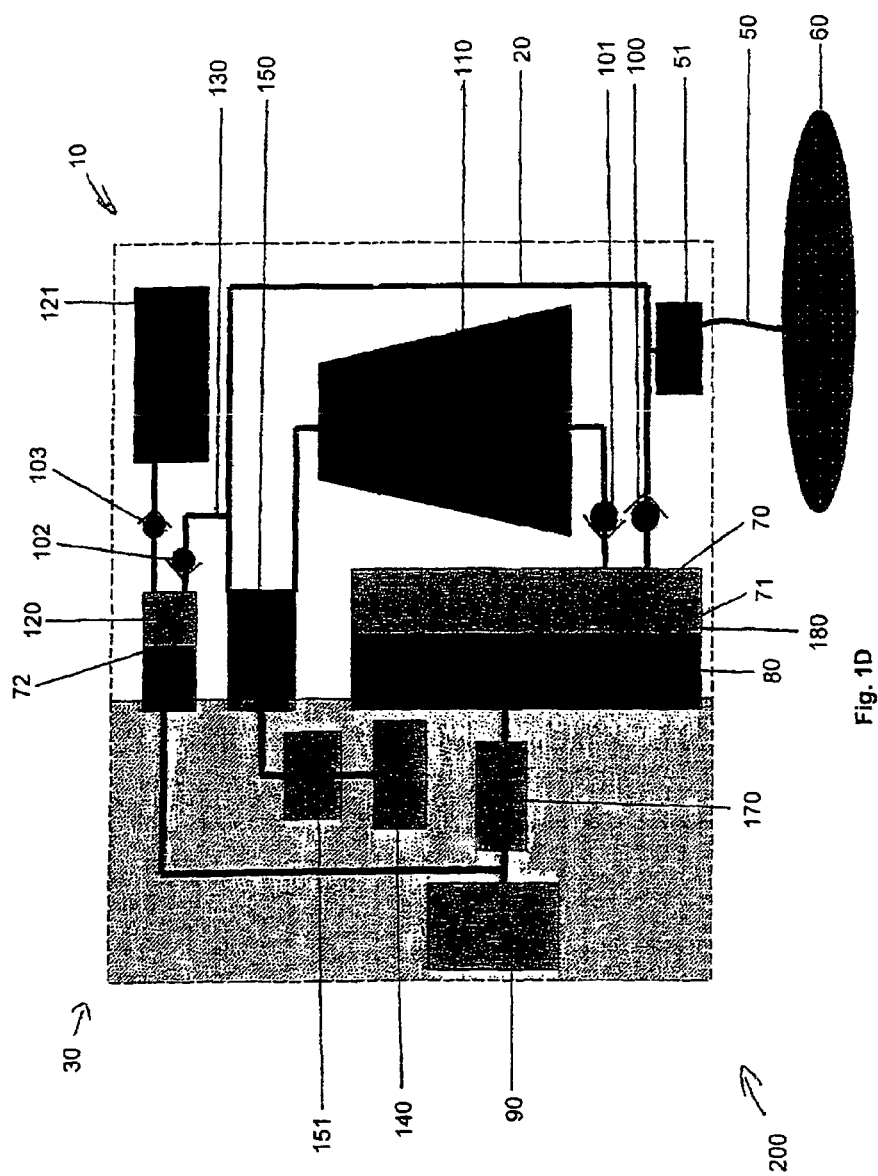
FIG. 1d is a schematic diagram of one embodiment of the disclosed dialysis device.

Referring to FIG. 1d, there is presented an alternative embodiment of the dialysis device according to the disclosure. The dialysis device (200) works in essentially the same way as the device described in FIGS. 1a-c. The regenerated dialysate from the sorbent zone (110) flows past a degasser in the form of a hydrophobic membrane (150). The external side of the membrane is subjected to negative pressure by a vacuum pump (151) in fluid communication with the hydrophobic membrane to aid the removal of gas generated during the dialysis procedure. Differing from 1a-c, the gas vented from the dialysate is then passed through an ammonia sensor (140) located in the control housing (30). The ammonia sensor monitors the level of ammonia in the gas vented from the dialysate to ensure that the ammonia level does not exceed a safe limit, prior to returning the dialysate to the peritoneal cavity (60) of a patient.

Figure 1E:
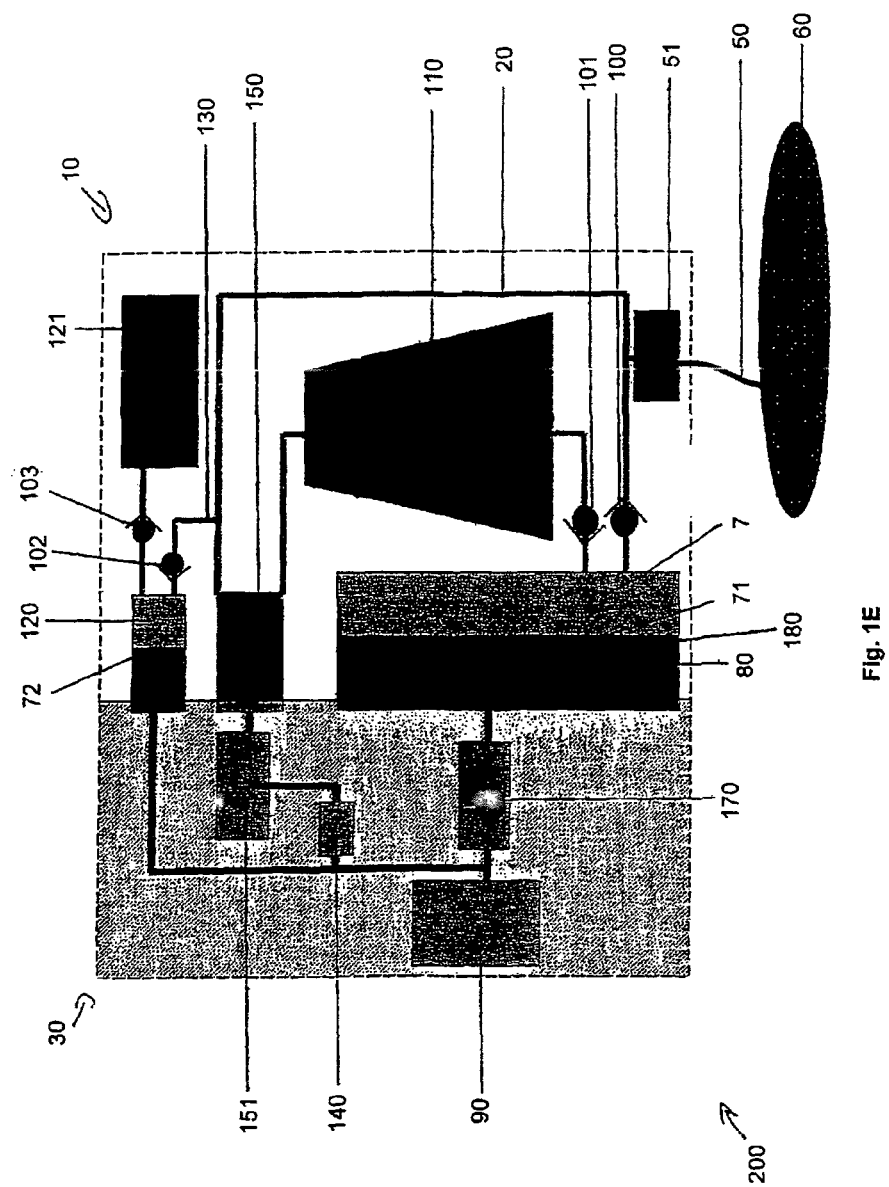
FIG. 1e is a schematic diagram of one embodiment of the disclosed dialysis device.

Referring to FIG. 1e, there is shown an alternative embodiment of the dialysis device according to the disclosure. The dialysis device (200) works in essentially the same way as the device described in FIGS. 1a-c. However, the pump (90) also subjects the hydrophobic membrane (150) via the conduit connector (not shown) and valve (104) to negative pressure during an outflow mode (where dialysate is received from a patient's peritoneal cavity (60) via a flexible dialysate tube (50)). Valve (104) ensures that no gas is introduced into the dialysate path via the hydrophobic membrane (150) during an inflow mode, when the pump (90) subjects the pressure chamber (80) to positive pressure. Ammonia gas released from the dialysate is then detected by the ammonia sensor (140).

Figure 1F:
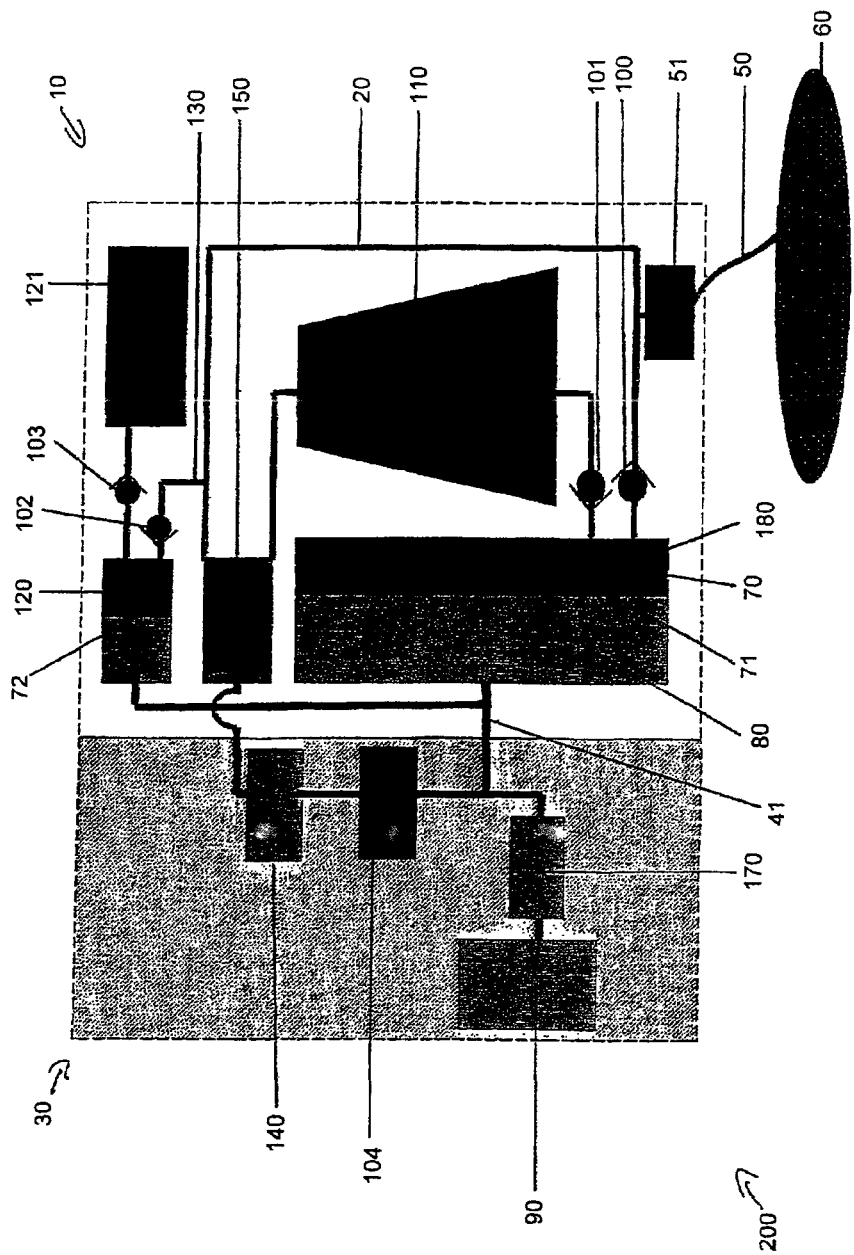
FIG. 1f is a schematic diagram of one embodiment of the disclosed dialysis device.

Referring to FIG. 1f, there is shown an alternative embodiment of the dialysis device according to the disclosure. The dialysis device (200) works in essentially the same way as the device described in FIGS. 1a-c. However, the pump (90) is in fluid communication with both the pressure chamber (80) and the enrichment module (120) via a single connection (41) in the disposable housing (10). The pump (90) also subjects the degasser in the form of a hydrophobic membrane (150) to negative pressure during an outflow mode (where dialysate is received from a patient's peritoneal cavity (60) via a flexible dialysate tube (50)). During an inflow mode the pump (90) subjects the pressure chamber (80) to positive pressure. Valve (104) ensures that no gas is introduced into the dialysate path via the hydrophobic membrane (150) during an inflow mode, when the pump (90) subjects the pressure chamber (80) to positive pressure. Ammonia gas released from the dialysate is then detected by the ammonia sensor (140).

Referring to FIG. 2a, there is presented an alternative embodiment of the flow system (201) in accordance with the present disclosure wherein the flow of the dialysate is toward the storage chamber (70) from the peritoneal cavity (60), i.e. outflow mode. The pump (90) actuates the deformable diaphragm (71), by inducing negative pressure in the pressure chamber (80). The negative pressure in the pressure chamber (80) deforms the deformable diaphragm (71) by biasing the deformable diaphragm (71) in the direction of arrow A and thereby moves dialysate from said peritoneal cavity (60) of the patient into the dialysate conduit (20) via bubble trap (51). The dialysate flows to the storage chamber (70) located in a rigid compartment (180) through check valve (100). A pressure sensor (170) is located in operable communication with the pump (90) to establish a preselected negative pressure within the pressure chamber (80) and to determine if the pressure of the dialysate being withdrawn from the peritoneal cavity (60) is within a safe limit.

The pump (90) operates intermittently under the control of the pressure sensor (170) to maintain the negative pressure in the pressure chamber (80) within a preselected range. Once the storage chamber (70) is full of dialysate, this is detected by the pressure sensor (170) which inverts the pump direction and converts the system to an inflow mode.

An enrichment module (120) is provided in fluid communication with the conduit (20) via a conduit (130). The enrichment module (120) is configured to be actuated by a syringe pump (91) in the inflow mode.

Referring to FIG. 2b, the flow system of FIG. 2a is shown in the inflow mode, wherein the flow of the dialysate is from the storage chamber (70) to the peritoneal cavity (60). Once the storage chamber (70) is full, the pump (90) actuates the deformable diaphragm (71), by inducing positive pressure in the pressure chamber (80). The positive pressure in the pressure chamber (80) deforms the deformable diaphragm (71) by biasing the deformable diaphragm (71) in the direction of arrow B and thereby moves dialysate from the storage chamber (70) and check valve (100) closes preventing dialysate from returning to the peritoneal cavity (60) before being treated to remove contaminants.

The pressure sensor (170) monitors the pressure in the pressure chamber (80) to ensure that the pressure of the dialysate being returned to the peritoneal cavity (60) in the inflow mode is within a safe limit.

The dialysate flows from the storage chamber (70) into the sorbent zone (110) through check valve (101). The regenerated dialysate from the sorbent zone (110) flows past a degasser in the form of a hydrophobic membrane (150) located upstream of a check valve (105). The presence of check valve (105) results in a positive pressure gradient across the hydrophobic membrane which permits the removal of any unwanted gas emitted during the dialysis operation. The dialysate then flows through an ammonia sensor (140) which monitors the level of ammonia in the regenerated dialysate, to ensure that the ammonia level does not exceed a safe limit, prior to returning to the peritoneal cavity (60) of a patient.

The regenerated dialysate then flows past an enrichment module (120). In the inflow mode, the syringe pump (91) actuates the enrichment module (120), which contains a volume of enrichment solution under positive pressure. The enrichment module (120) then dispenses a preselected amount of enrichment solution containing desired substances, such as electrolytes, osmotic agents, nutrients, medication and the like, into the dialysate conduit (20) via conduit (130). The syringe pump (91) only operates in the inflow mode.

The regenerated dialysate then flows back to the peritoneal cavity (60) through the bubble trap (51) and flexible dialysate conduit (50).

As in the outflow mode, the pump (90) is operated intermittently under the control of the pressure sensor (170) to maintain the positive pressure in the pressure chamber (80) within a preselected range. Once the storage chamber is empty of dialysate, the pressure sensor (170) detects this and inverts the pump direction and converts the system to the outflow mode to repeat the dialysis cycle.

Figure 3:
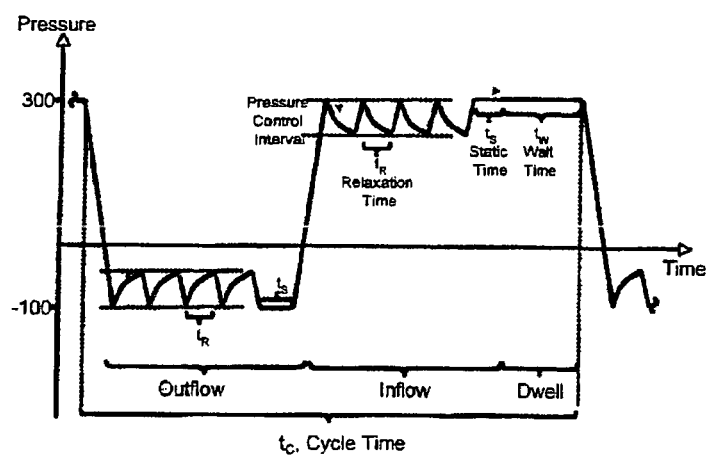
FIG. 3 is a graphic representation of the flow control of the dialysate according to an embodiment of the present disclosure.

FIG. 3, shows a graphic representation of the flow control of dialysate in an embodiment of the dialysis device according to the present disclosure. The phases of the flow control in FIG. 3 are separated into "outflow, "inflow" and "dwell".

In an outflow mode, a negative actuating pressure is produced by a pump, which is operated intermittently under the control of a pressure sensor. As can be seen in FIG. 3, the negative pressure in the pressure chamber is maintained within the limits of a preselected upper and lower pressure. Unobstructed flow of dialysate is indicated by continuous (rapid) relief of (negative) pressure during the off-times of the pump. The measurement of the time which passes during the pressure relief ($t_R$—relaxation time) may be used to estimate the effected fluid flow speed. When the storage chamber is full of dialysate, the pressure cannot be relieved anymore and the pressure becomes static for a period of time ($t_S$—static time). This is detected by a pressure sensor, which triggers the reversal of the pump to an inflow mode. The average "outflow" flow rate is equal to the volume of the storage chamber ("tidal volume") divided by the time required to fill the storage chamber completely. This rate is dependent on the choice of preselected pressure limits and can be modified accordingly.

During the inflow mode a positive actuating pressure is produced by the pump. The dialysate contained in the storage chamber is subsequently forced through the sorbent zone of the device and is then returned to the patient. The pump is operated intermittently, such that the positive pressure is regulated between preselected upper and lower pressure limits. The fluid in the storage chamber is forced through the sorbent cartridge, thereby relieving the (positive) pressure. The duration of this relief can be used to estimate the flow rate ($t_R$—relaxation time). When the pump chamber is empty, the pressure cannot be relieved anymore and the pressure becomes static for a period of time ($t_S$—static time), indicating completion of the "inflow" phase. The average "inflow" flow rate equals the volume of the storage chamber divided by the time required to complete "inflow".

FIG. 3 also shows a wait time or "dwell" time ($t_w$). This period is used to control the overall fluid exchange rate: overall flow rate equals storage chamber volume (tidal volume) divided by the total cycle time ($t_c$=outflow+inflow+dwell). For example, if a specific overall exchange rate is desired, then the system can use the dwell time as a flexible wait time until the desired total cycle time has passed.

Figure 4A:
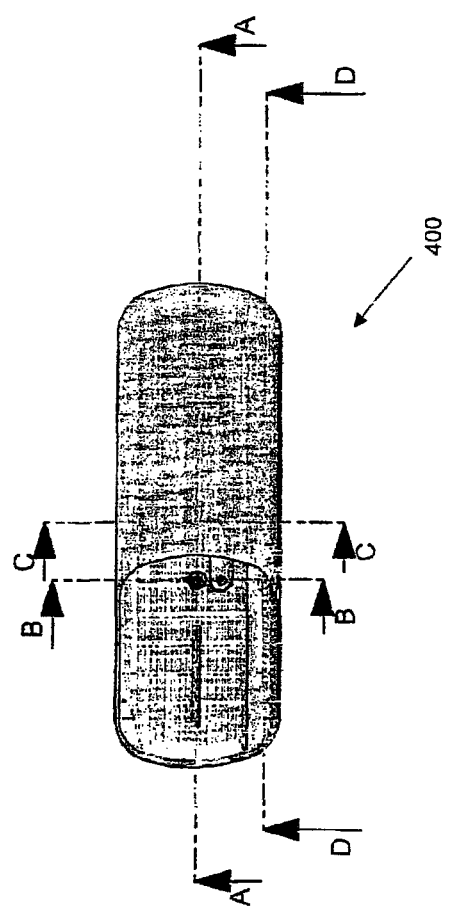
Figure 4B:
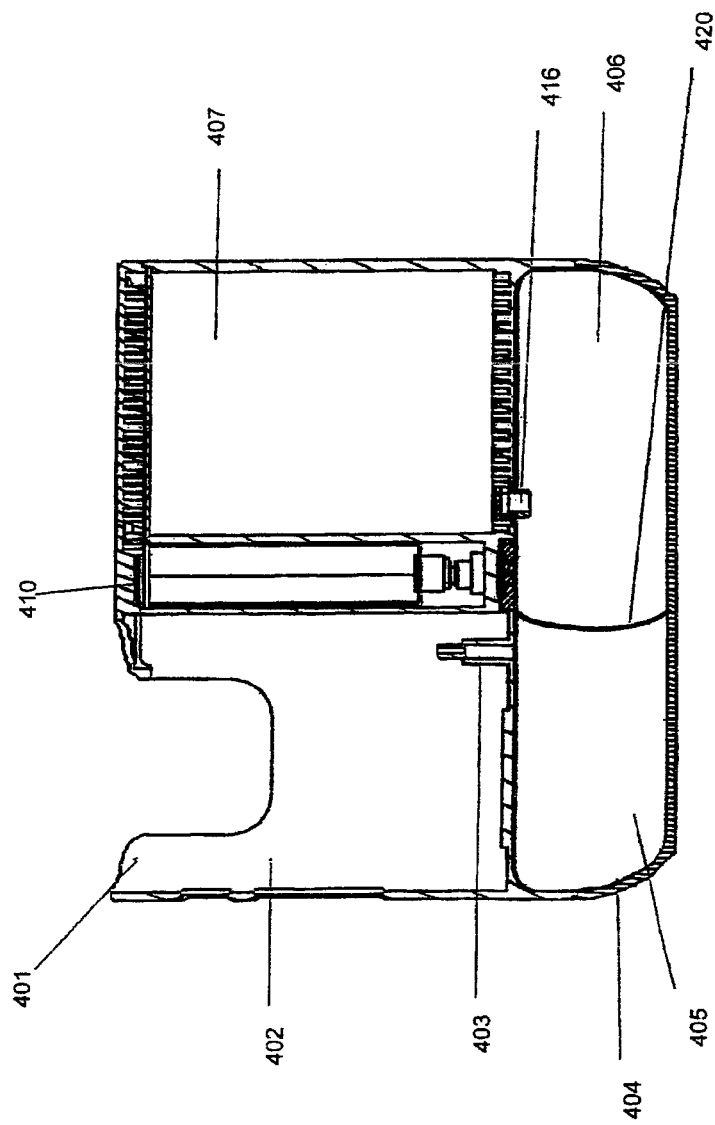

FIG. 4a shows a prototype disposable housing (400) in accordance with an embodiment of the present disclosure. FIG. 4b shows a cross sectional view of the disposable housing taken along axis A-A of FIG. 4a. The disposable housing comprises an enclosure (401) defining an interior (402) for receiving a control housing (not shown) via a conduit connector (403). The disposable housing comprises a rigid compartment (404) defining a pressure chamber (405) in which a storage chamber (406) is disposed. The storage chamber has a deformable diaphragm (420) integrally formed in a wall thereof. The storage chamber (406) is in fluid communication with a sorbent zone (407), via a fluid channel (416).

The sorbent zone (407) comprises a check valve (409, see FIGS. 4c and 4d) in fluid communication with a degasser in the form of a hydrophobic membrane (410).

Figure 4C:
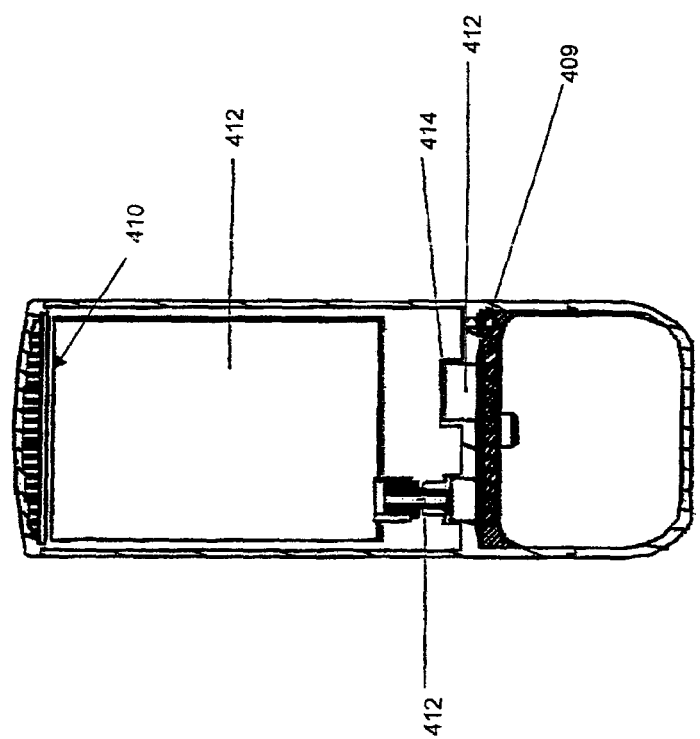

FIG. 4c provides a cross-sectional view of the sorbent module along axis C-C of FIG. 4a. An enrichment module (411) is in fluid communication with an enrichment solution reservoir (412) via a check valve (413). The enrichment module (411) is also in fluid communication with the conduit of dialysate via check valve (414).

FIG. 4d provides a cross-sectional view of the sorbent module along axis D-D of FIG. 4a. The regenerated dialysate exits the disposable housing via check valve (409) and outlet (415).

In use during an outflow mode, the control housing (not shown) is located in the interior (402) of the disposable housing (400, see FIGS. 4a and 4b). The pump in the control housing actuates the deformable diaphragm (420) located in the wall of the storage chamber (406), via the conduit connector (403, see FIG. 4b) by transmitting pump fluid from the conduit connector (403) thereby inducing negative pressure in the pressure chamber (405). The negative pressure in the pressure chamber (405) moves dialysate from the peritoneal cavity of the patient into the storage chamber (406) through check valve (408). At the same time as the storage chamber (406) is actuated under negative pressure, the enrichment module (411, see FIG. 4c) is also actuated under negative pressure by the pump such that a predetermined amount of an enrichment solution is withdrawn from an enrichment solution reservoir (412) though check valve (413) into the enrichment module (411).

In use during the inflow mode once the storage chamber (406) is full, the pump actuates the deformable diaphragm (420) located in the wall of the storage chamber (406) via the conduit connector (403) by transmitting fluid to the conduit connector (403) and thereby inducing positive pressure in the pressure chamber (405). The positive pressure in the pressure chamber (405) moves dialysate from the storage chamber (406) and check valve (408) closes preventing dialysate from returning to the peritoneal cavity before being treated to remove contaminants. Dialysate flows from the storage chamber (406) into the sorbent zone (407) through channel (416). The regenerated dialysate exiting from the sorbent zone (407) flows past a hydrophobic membrane (410) to remove any unwanted gas emitted during the dialysis operation. The degassed dialysate then flows past an enrichment module (411), a check valve (409) and exits the disposable housing via tube connector (415).

In the inflow mode, the pump also actuates the enrichment module (411) under positive pressure and check valve (413) closes. The enrichment module (411) dispenses a preselected amount of enrichment solution containing desired substances, such as electrolytes, osmotic agents, nutrients, medication and the like, into the dialysate through check valve (414). The dialysate is then returned to the peritoneal cavity via a check valve (409) and a tube connector (415).

Figure 5:
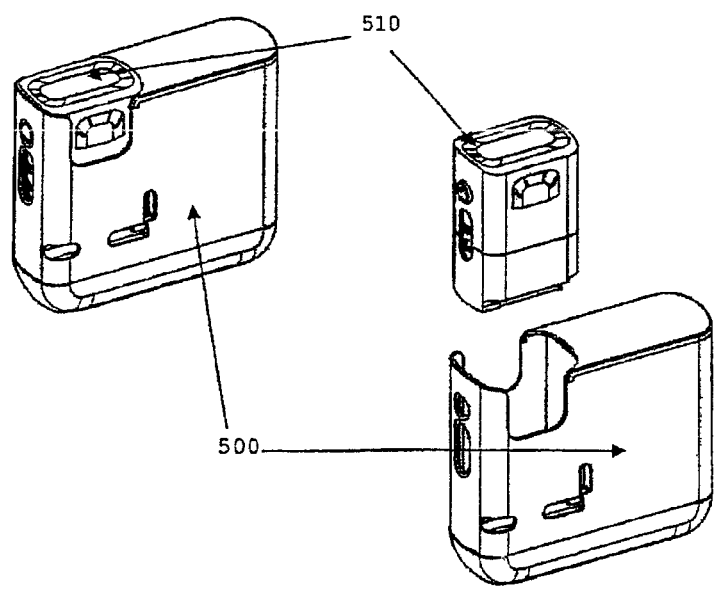
FIG. 5 is a perspective view of a prototype of one embodiment of the dialysis device disclosed.

Referring now to FIG. 5, there is shown a picture of a prototype of one embodiment of the entire flow system disclosed herein, with a disposable housing (500) and the control housing (510).

Figure 6:
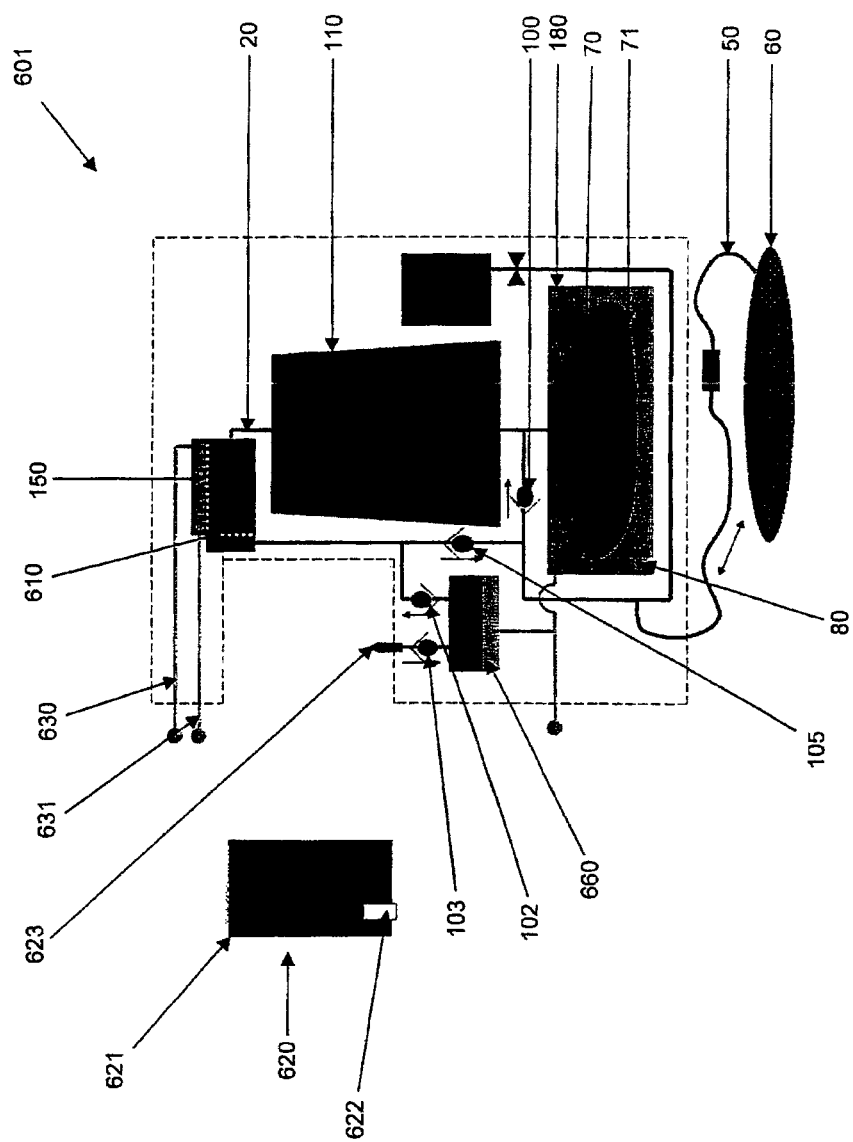
FIG. 6 is a schematic diagram of one embodiment of the disclosed disposable housing comprising a discrete additive dispensing means.

Referring to FIG. 6, there is shown one embodiment of a disposable housing (601) having a flow path in the form of conduit (20). The disposable housing (601) comprises a flexible dialysate tube (50) which is capable of being in fluid communication with the peritoneal cavity (60) and a conduit (20). The dialysis device further comprises a storage chamber (70) located in a rigid compartment (180). The storage chamber (70) comprises a deformable diaphragm (71) integrally formed in one of the walls of the storage chamber (70). The deformable diaphragm (71) is in fluid communication on one side with the dialysate conduit (20) and, on another opposite side, in fluid communication with a pressure chamber (80).

The pump (670) is configured to actuate the deformable diaphragm (71), by inducing a pressure change in the pressure chamber (80) which deforms the deformable diaphragm (71) and thereby moves dialysate within said dialysate conduit (20).

Check valves (100,102,103,105) are disposed along the conduit (20) and are configured to, in the outflow mode, allow the dialysate to flow from the peritoneal cavity (60) to the storage chamber (70), and in the inflow mode allow the dialysate to flow from the storage chamber (70) to said sorbent zone (110) for removal of contaminants therein, and further permit the dialysate substantially free of said contaminants to flow back to the peritoneal cavity (60).

The disposable housing is also provided with a discrete enrichment module (620), for dispensing a preselected amount of an enrichment solution into the dialysate. The enrichment module is not in fluid communication with the dialysate flow path in this figure. The enrichment module comprises an enrichment solution reservoir (621), a container in the form of a bag manufactured from a biocompatible material for holding the enrichment solution (not shown). The enrichment module (620) is provided with a connector (622) adapted for fluid communication with the dialysate conduit (20) of the disposable housing (601). The connector (622) is sealed prior to insertion into the disposable housing to maintain the sterility of the enrichment solution in the enrichment module (620). The disposable housing is provided with a male connector (623) of complementary configuration to the connector (622) located on the enrichment module (620). When in mating engagement (see FIG. 7) the male connector (623) serves to break the seal of the connector (622) to form a fluid connection between the enrichment reservoir (621) in the enrichment module (620) and the dialysate conduit (20) of the disposable housing (601).

The disposable housing (601) also comprises an enrichment pump (660) for adding a predetermined amount of enrichment solution to the dialysate conduit (20).

A degasser in the form of a hydrophobic membrane (150) is also located downstream of the sorbent zone (110). The external side of the hydrophobic membrane (150) is in fluid communication with air conduits (630 and 631).

A hydrophilic membrane (610) is disposed in the degasser compartment, in the dialysate flow path and directly downstream of the hydrophobic degasser membrane (150). The hydrophilic membrane (610) serves as a barrier to prevent gas, particles and bacteria contained in the dialysate exiting the sorbent zone (110) from reaching the peritoneal cavity (60). The membrane also produces a backpressure facilitating the venting of gas through the degasser membrane (150).

Figure 7:
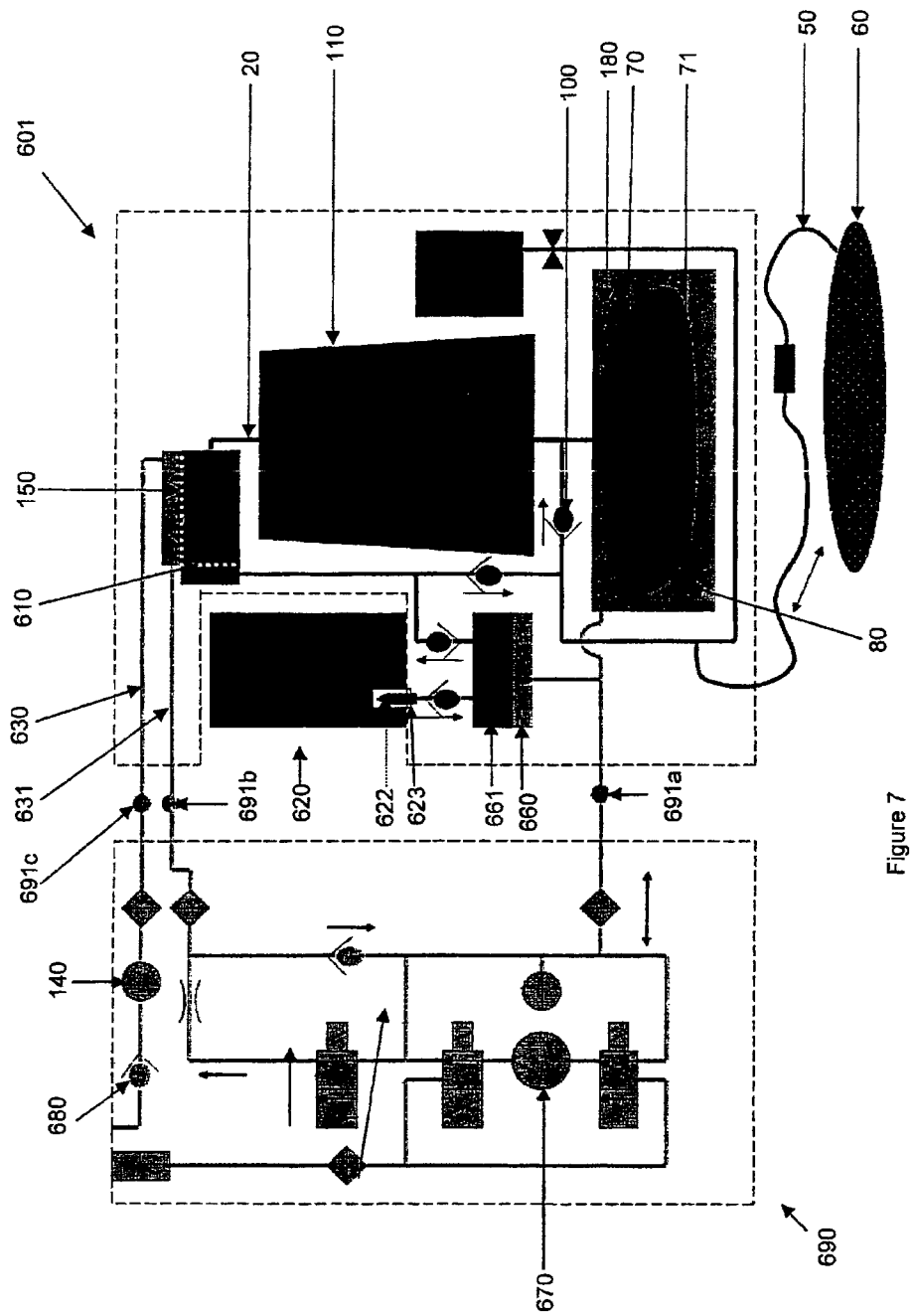
FIG. 7 is a schematic diagram of one embodiment of the disclosed dialysis device comprising a discrete additive dispensing means in locking engagement with a disposable housing in accordance with the disclosure.

Referring to FIG. 7, there is shown an embodiment of the disclosed dialysis device (700). The dialysis device comprises a disposable housing (601) having a flow path in the form of conduit (20), a controller in the form of a control housing (690) for controlling the operation of the disposable housing (601). The disposable housing (601) and control housing (690) comprise interface means in the form of conduit connectors (691a, 691b, 691c) that connect the control housing (690) and the disposable housing (601). The disposable housing (601) and control housing (690) are brought into operative engagement when the conduit connectors are brought into locking engagement. The conduit (20) of the disposable housing (601) is fluidly sealed from the control housing (690) and conduit connectors (691a, 691b, 691c).

The dialysis device (700) comprises a flexible dialysate tube (50) which is capable of being in fluid communication with the peritoneal cavity (60) and a conduit (20). The dialysis device further comprises a storage chamber (70) located in a rigid compartment (180). The storage chamber (70) comprises a deformable diaphragm (71) integrally formed in one of the walls of the storage chamber (70). The deformable diaphragm (71) is in fluid communication on one side with the dialysate conduit (20) and, on another opposite side, in fluid communication with a pressure chamber (80). When the disposable housing (601) and control housing (690) are operably coupled to each other, the conduit connector (691a, 691b, 691c) fluidly couples the pressure chamber (80) of the disposable housing (601) to an air pump (670) located in the control housing (690).

The air pump (670) is configured to actuate the deformable diaphragm (71), by inducing a pressure change in the pressure chamber (80) which deforms the deformable diaphragm (71) and thereby moves dialysate within said dialysate conduit (20).

Check valves (100,102,103,105) are disposed along the conduit (20) and are configured to, in the outflow mode, allow the dialysate to flow from the peritoneal cavity (60) to the storage chamber (70), and in the inflow mode allow the dialysate to flow from the storage chamber (70) to said sorbent zone (110) for removal of contaminants therein, and further permit the dialysate substantially free of said contaminants to flow back to the peritoneal cavity (60).

In this figure the discrete enrichment module (620), is located in the disposable housing (601). The connector (622) of the enrichment module (620) is in mating engagement with the male connector (623) of the disposable housing to form a fluid connection between the enrichment reservoir (621) in the enrichment module (620) and the dialysate conduit (20) of the disposable housing (601).

The disposable housing (601) also comprises an enrichment pump (660) for adding a predetermined amount of enrichment solution to the dialysate conduit (20). The enrichment pump (660) is a fixed displacement pump comprising a diaphragm (661) in fluid communication with the air pump (670). The air pump (670) exerts a positive or a negative air pressure to the diaphragm (661) of the enrichment pump (660) and the deformable diaphragm (71) of the storage chamber (70), functioning as pneumatic pump for cycling dialysate through the dialysate conduit (20) at the same time. On one side of the diaphragm (661) in the enrichment pump (660) is an air compartment which fluidly connects to the air pump (670), and the other side is the enrichment solution compartment connecting to the enrichment reservoir (621) reservoir via the mated connectors (622,623). When the enrichment solution compartment is subjected to negative pressure enrichment solution is drawn from the enrichment reservoir (621). When a positive pressure is applied to the air compartment, the enrichment solution is forced out of the enrichment pump (660) into the dialysate conduit (20).

A degasser in the form of a hydrophobic membrane (150) is also located downstream of the sorbent zone (110). The external side of the hydrophobic membrane (150) is in fluid communication with air conduits (630 and 631). In a normal dialysis operation, air conduit (630) is an outlet to the ammonia sensor (140) and air conduit (630) is in fluid communication with the air pump (670). During degassing, the air pump (670) in the control housing (690) exerts a negative pressure to remove any gas from the dialysate in the dialysate conduit (20). A check valve (680) prevents external air from entering air conduit (630).

A hydrophilic membrane filter (610) downstream of the hydrophobic membrane (150) prevents gas, particles and bacteria contained in the dialysate from reaching the peritoneal cavity (60). The membrane (610) also produces a backpressure facilitating the venting of gas through the hydrophobic membrane (150).

Figure 8A:
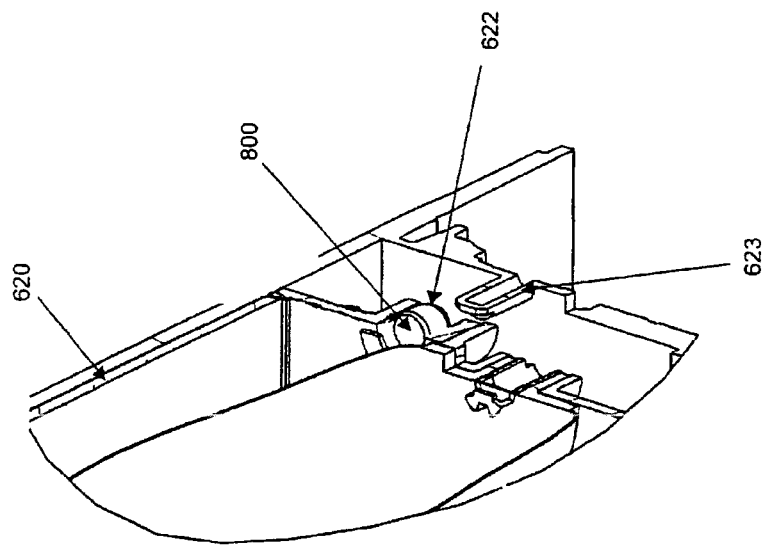
FIG. 8 is a cross sectional view of a sealed connector of the additive dispensing means in accordance with the disclosure.
Figure 8B:
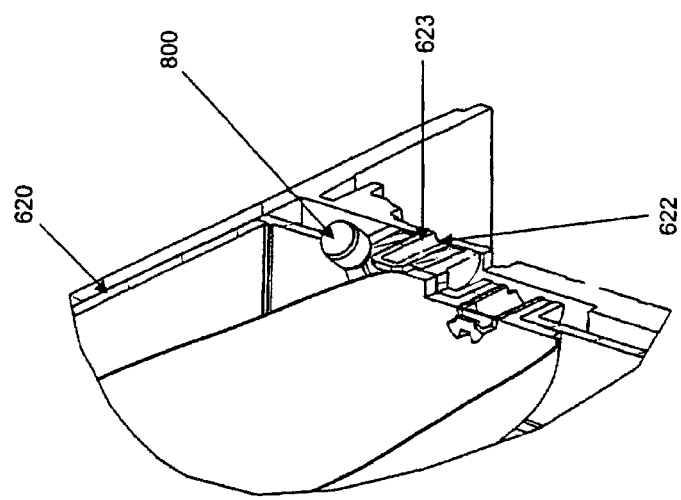

FIGS. 8a and 8b show an embodiment of a sealed connector (622) in accordance with the present invention. The connector (622) on the enrichment module (620) is provided with a plug (800) that can be dislodged by the connector (623) located on the disposable housing (601). In FIG. 8b the connector (622) on the enrichment module is brought into mating engagement with the connector (623) on the disposable housing (601) to dislodge the plug (800).

FIGS. 9a and 9b show an embodiment of a sealed connector (622) in accordance with the present invention. The connector (622) on the enrichment module (620) is provided with a plug (800) that can be pierced by the connector (623) located on the disposable housing (601). In FIG. 8b the connector (622) on the enrichment module is brought into mating engagement with the connector (623) on the disposable housing (601) to pierce the plug (800).

FIGS. 10a and 10b show the embodiment of a sealed connector of FIGS. 9a and 9b. The connector (622) on the enrichment module (620) is provided with a plug (800) that can be pierced by the connector (623) located on the disposable housing (601). In FIG. 10b the connector (622) on the enrichment module is brought into mating engagement with the connector (623) on the disposable housing (601) to pierce the plug (800). The enrichment module is a rigid container for holding the additive solution, comprising a sponge (1001) located at an end of the container in communication with a connector (622). The sponge facilitates delivery of the enrichment solution from the enrichment reservoir (621) to the dialysate conduit (20).

Figure 11:
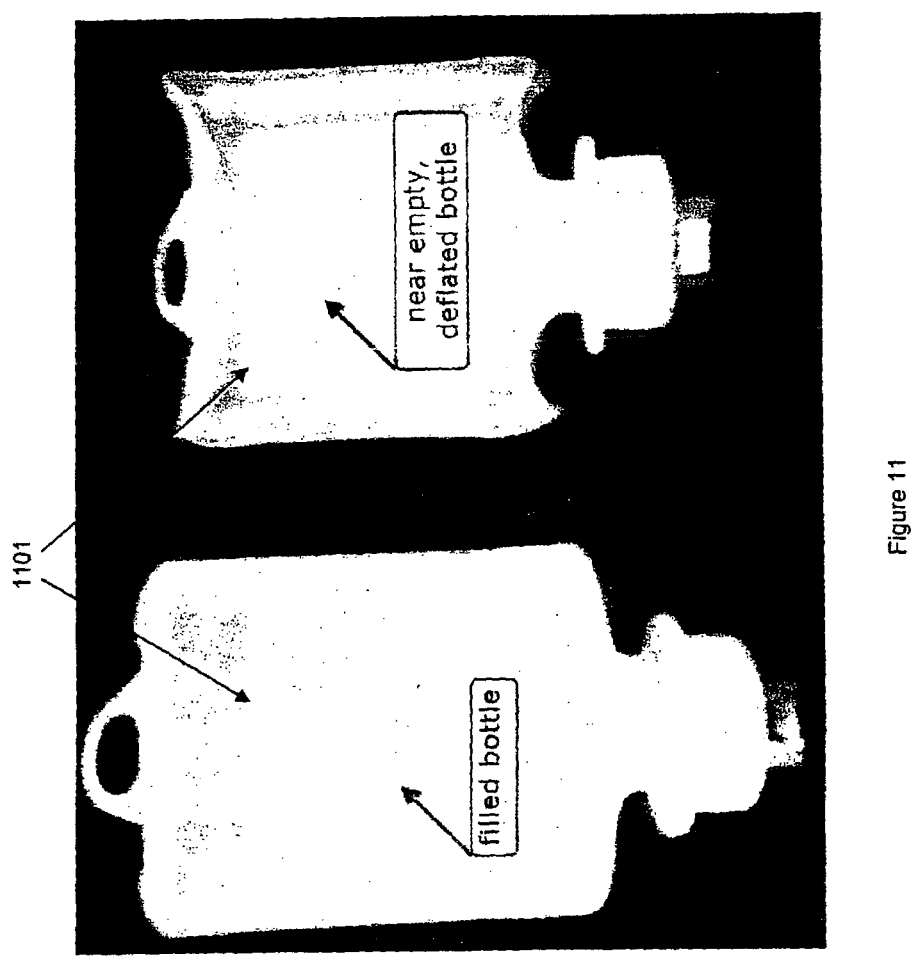
FIG. 11 is a cross sectional view of an embodiment of an additive dispensing means in accordance with the disclosure.

FIG. 11 shows another embodiment of a container in the enrichment module (620). In this figure the container is in the form of a resiliently deformable bottle (1101). The bottle on the left hand side is full of enrichment solution. The bottle on the right hand side of the figure is depleted.

Figure 12A:
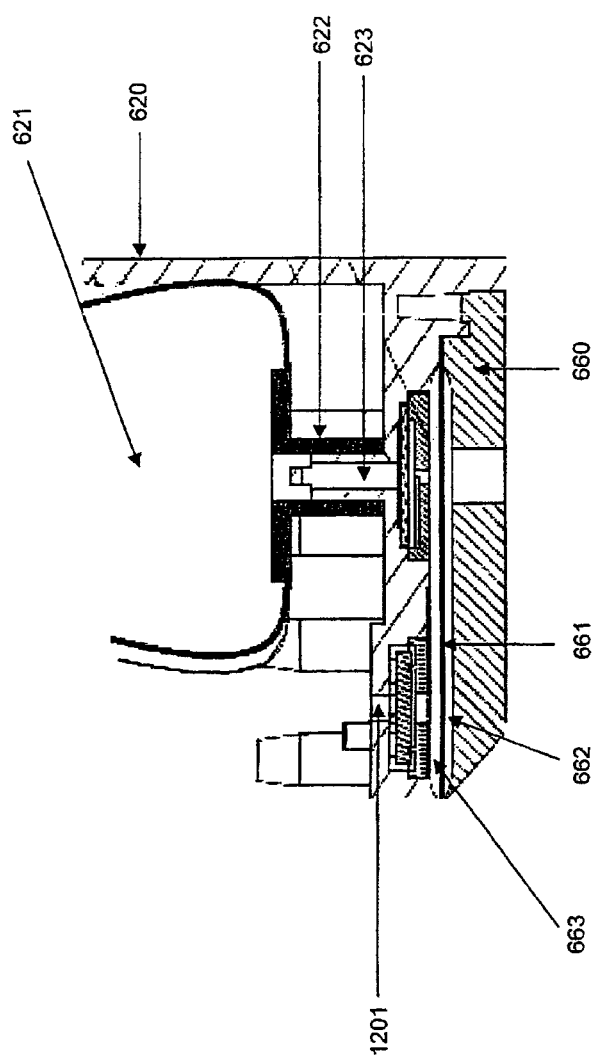
FIG. 12a-c is a cross sectional view of an embodiment of an automatic dispensing system in accordance with the disclosure.

FIG. 12a shows a cross-sectional view of the enrichment pump (660). The enrichment module (620) comprises an enrichment reservoir (621) in fluid communication with the enrichment pump (660) via the mated connectors (622 and 623). The enrichment pump (660) is provided with a diaphragm (661) which defines an air chamber (662) in fluid communication with the air pump (not shown) and an enrichment solution chamber (663) in fluid communication with the enrichment reservoir (621).

Figure 12B:
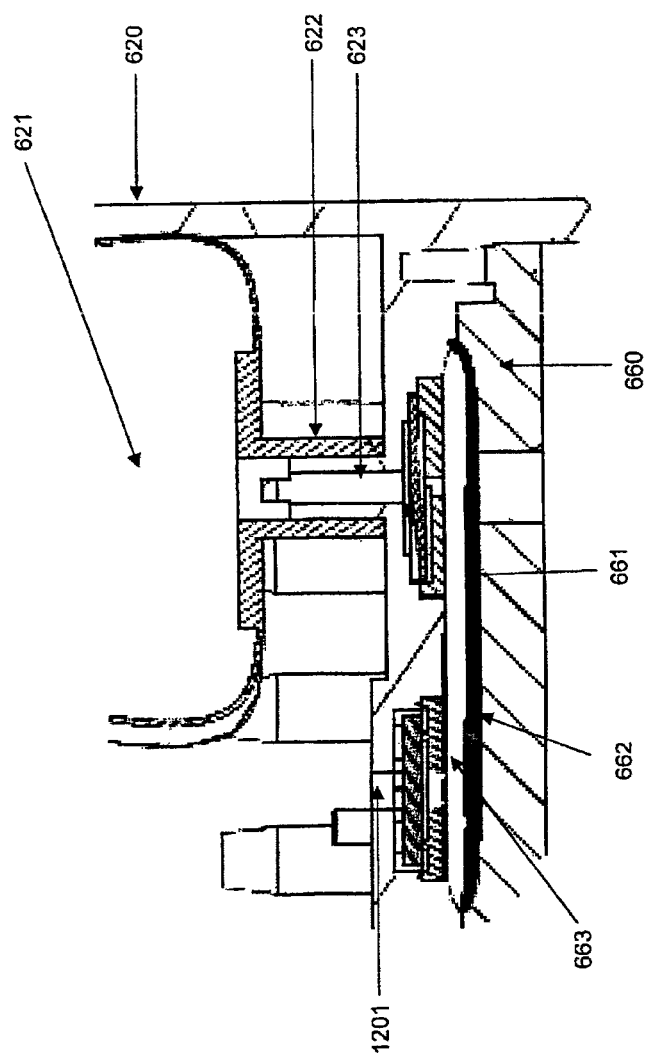

FIG. 12b shows a close up view of FIG. 12a in an outflow cycle. When the air pump exerts a negative pressure beyond 50 mmHg, in the dialysate outflow cycle, enrichment solution is drawn from the enrichment reservoir (621) into the enrichment solution chamber (663) of the enrichment pump (660).

Figure 12C:
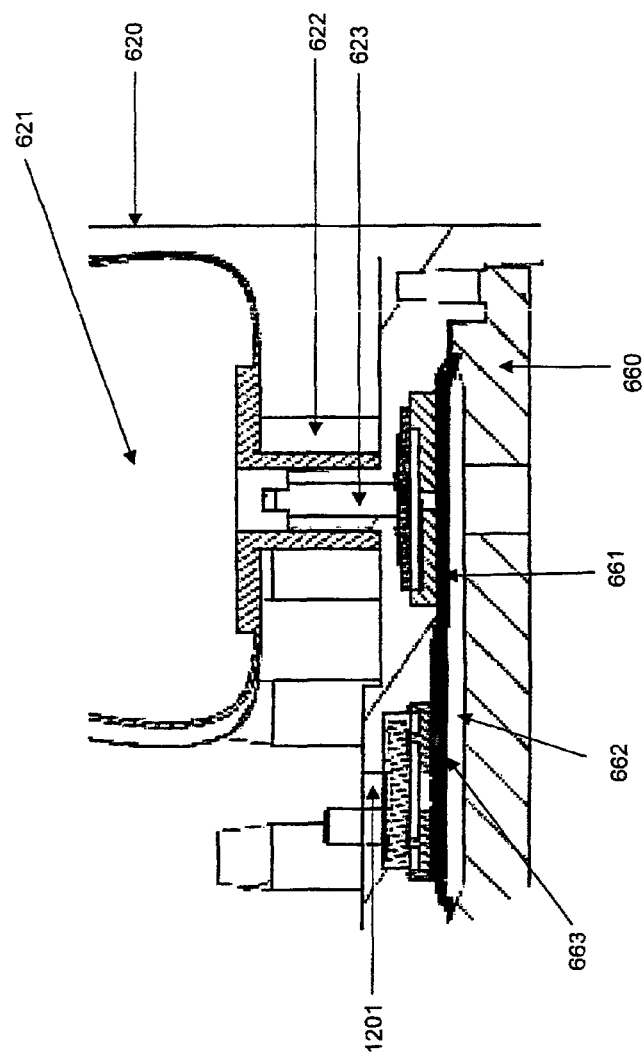

FIG. 12c shows the enrichment pump (660) in an inflow cycle. In the inflow cycle when a positive pressure greater than 200 mmHg is exerted in the air chamber (662), the enrichment solution chamber (663) will be emptied and a fixed volume of enrichment solution, VEP, will flow to and merge with the dialysate in the dialysate conduit via outlet (1201).

Figure 13:
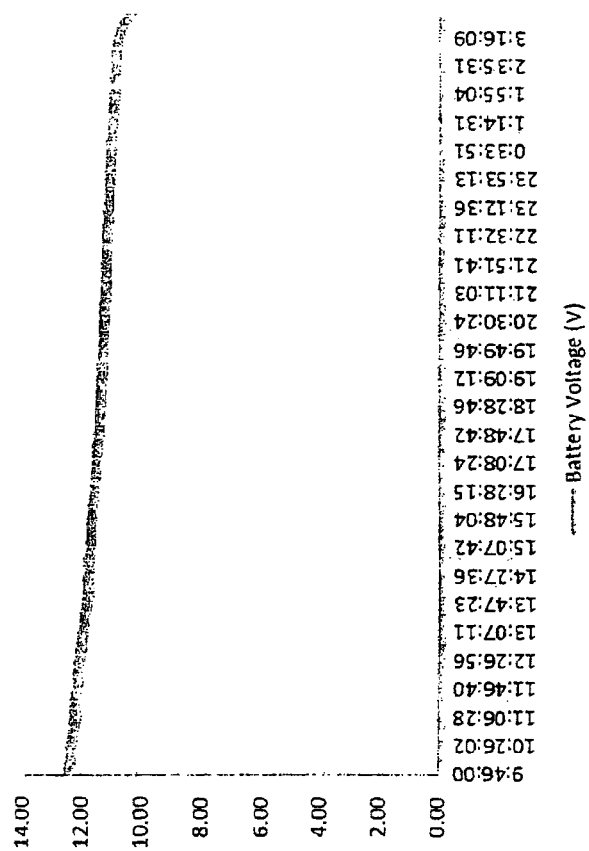
FIG. 13 is a graphic representation of the voltage drop of a rechargeable battery versus dialysis time in a dialysis device in accordance with the disclosure.
Figure 14:
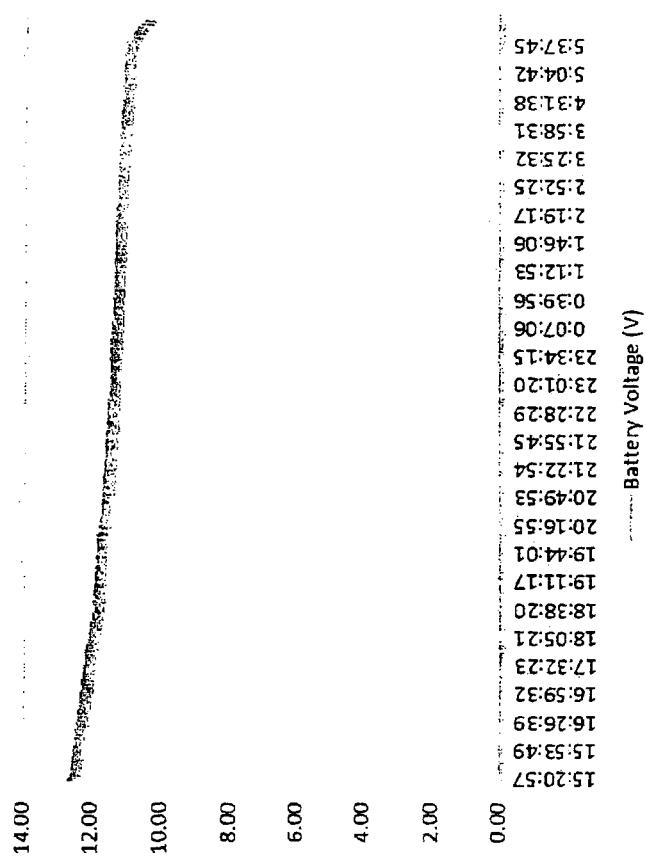
FIG. 14 is a graphic representation of the voltage drop of a rechargeable battery versus dialysis time with constant pumping in a device in accordance with the disclosure.

FIGS. 13 and 14 show the results of battery tests on a dialysis device in accordance with the disclosure. The purpose of the experiment was to determine the minimum capacity of the battery that is needed to support the operation of a high capacity dialysis cartridge for at least 12 hours. Based on an average power consumption of 153 mA of the system, for a 12 hour operation, the minimum battery capacity needed would be at least 1836 mAh. Thus, to retain at least 80% of the battery capacity over a year, the minimum battery needed will be 2203 mAH. This is according to the retentive specifications of the battery, where the battery capacity will drop to 80% of its overall capacity when its operation cycle is more than 300 cycles (1836 mAh×120%). To determine the actual usage duration for the system, 2 tests were performed using an 11.1V, 2250 mAH, Lithium Polymer battery.

Test #1:

Taking a representative operation scenario for a normal flow control, where the pump is being turned ON and OFF to maintain at either 400 mmHg (Inflow) or −100 mmHg (Outflow), without a relaxation of the pressure, the result showed that a 2250 mAh capacity battery was able to support the mentioned operation for 18 Hrs before it was shut down by the firmware at 10.5V. FIG. 13 shows the graph showing the voltage drop of the battery versus the operation time in this experiment.

Test #2:

In the second test, assuming the worst case scenario that the pump is constantly ON for the whole inflow and outflow cycle operation, the results show that the battery can last for 14.5 Hrs before it was shut down by the firmware at 10.5V. Below is the graph showing the voltage drop of the battery versus the operation time in this experiment.

Figure 15A:
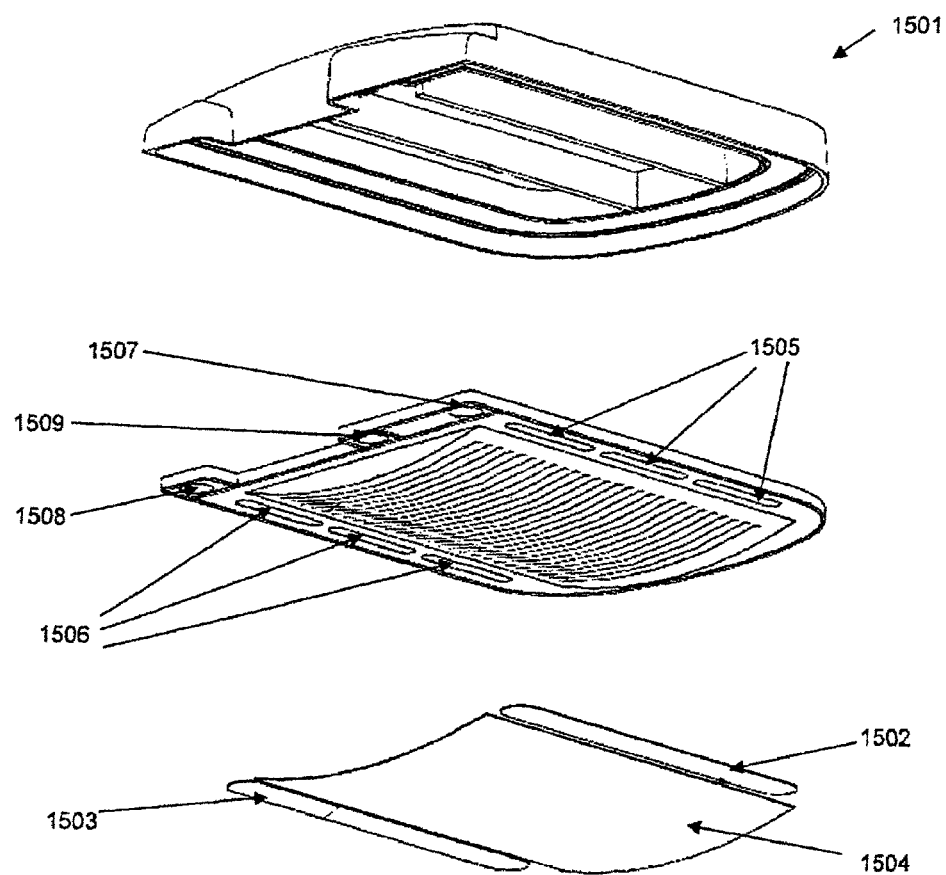
FIG. 15 is an embodiment of a degasser in a device in accordance with the disclosure.

FIG. 15a shows an exploded view of a degasser (1501) in accordance with the disclosure. The degasser comprises a gas vent means in the form of two hydrophobic membranes (1502) and (1503). The hydrophobic membranes are arranged in parallel on either side of a hydrophilic membrane (1504). Each hydrophobic membrane (1502 and 1503) is located adjacent to air vents (1505 and 1506). The degasser is also provided with air inlets/outlets (1507 and 1508) and a dialysate outlet (1509). The hydrophilic membrane is curved to facilitate the flow of gas in the dialysate to the hydrophobic membranes and subsequently the air vents to remove gas from the dialysate in the dialysate conduit of the dialysis device. In use a 4 micro paper filter seals the top of the sorbent zone in the dialysis device and is covered by the degasser. The hydrophilic membrane is located adjacent to the paper filter by a spacer (not shown). The hydrophilic membrane reduces sorbent powder leakage from the sorbent zone and paper filter and also acts as a bacterial filter.

Figure 15B:
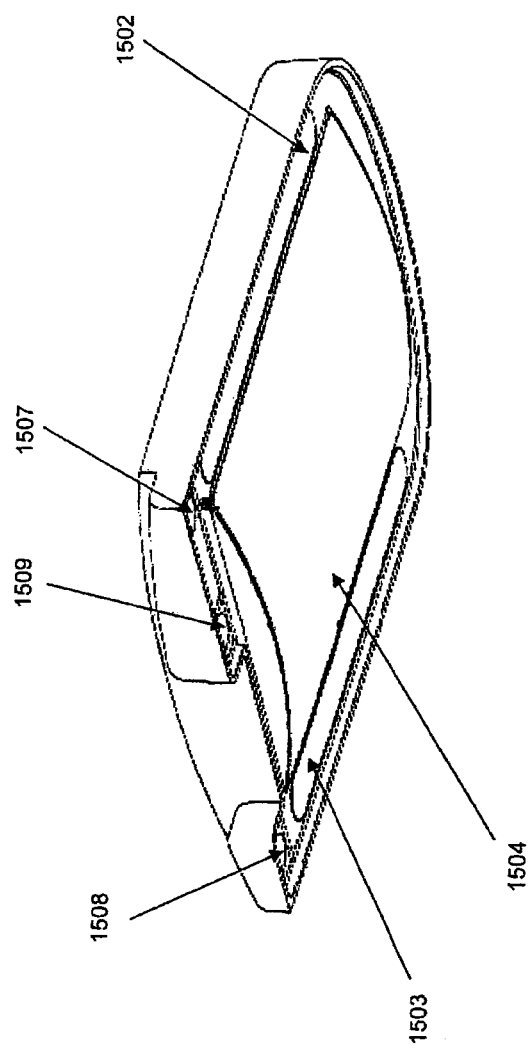

Referring to FIG. 15b, in a normal dialysis operation, a first air outlet (1507) is in fluid communication with an ammonia sensor and a second air outlet (1508) is in fluid communication with a degassing exhaust via another connecting air-port (not shown). When detecting for ammonia gas presence in the case of sorbent cartridge exhaustion, atmospheric air flows through a throttle valve, or any stable flow constrained valves, in the controller, allowing a controlled amount of air to flow through the first air outlet (1507), to an air conduit above the hydrophobic membranes, and flow out from the other end of the air conduit to the second air outlet (1508), and circulate to an ammonia sensor in the controller. During degassing, the air pump in the controller exerts a negative pressure to remove any gas, in particular $CO_2$, in the air conduit via the first air outlet (1507) back to an exhaust in the controller.

Figure 16:
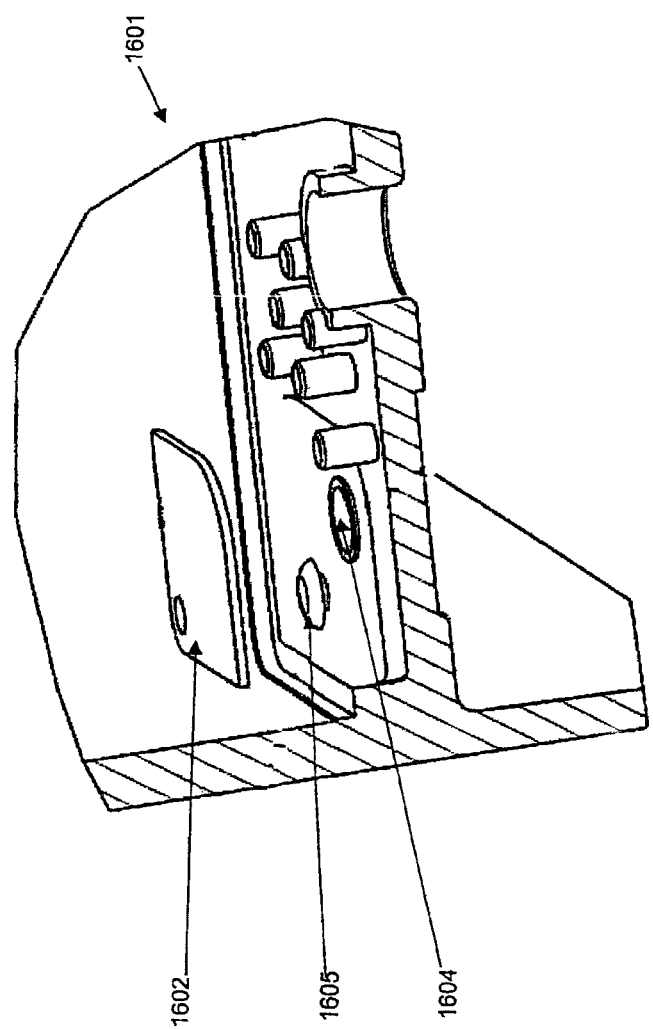
FIG. 16 is an embodiment of a fibrin trap in a device in accordance with the disclosure.

Referring to FIG. 16, an exploded view of a fibrin trap (1601) is shown. During dialysis, it is possible that dialysate will contain some small amount of fibrin. The trap comprises an inlet valve (1602) and a filter (not shown) located opposite the inlet valve (1602). The inlet valve is in the form of a resiliently deformable disk hinged on a stud (1605) such that the hinge is located away from the dialysate flow into the trap and thus will not catch on any fibrin present in the dialysate. In use the dialysate enters the trap through an inlet (1604) and passes through the disk valve (1602). The disk valve is located on a stud (1605). During an outflow mode, the disk valve (1602) is closed against the inlet (1604) preventing the flow of dialysate from the sorbent zone to the patient. The dialysate that enters the sorbent zone may comprise fibrin. The fibrin is prevented from entering the sorbent zone by the filter (1603) and is therefore retained in the trap (1601).

Figure 17:
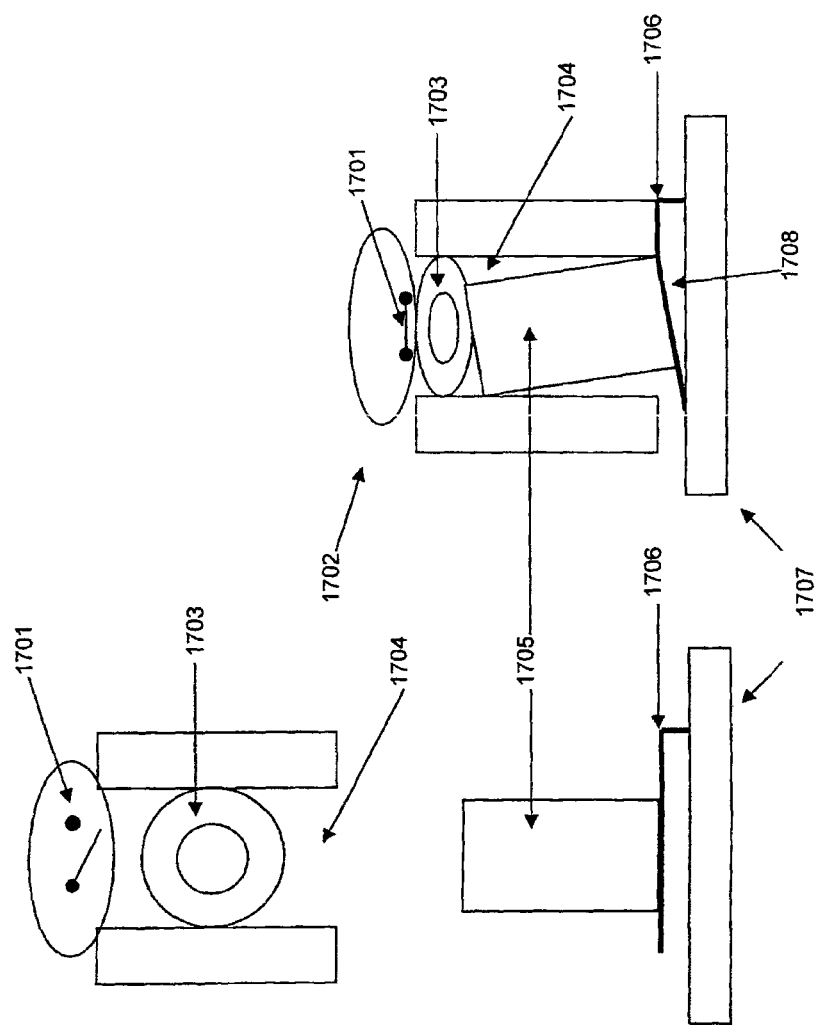
FIG. 17 is an embodiment of a power-connecting switch in accordance with the disclosure.

FIG. 17A shows a power-connecting switch in accordance with an embodiment of an invention. The switch (1701) is located in the controller (1702). The switch is in an open condition when the controller (1702) is not coupled to a disposable housing. A resiliently deformable material, in the form of a rubber tube (1703), is located in a channel (1704), immediately adjacent to the switch (1701).

A pin (1705) is located on a breakable frame (1706) on the disposable housing (1707), which is of complementary configuration to the channel (1704) located on the controller (1702). When the disposable housing and controller are coupled together, the pin (1705) is received in the channel (1704) and the frame is deformed and broken (1708) by the controller (1702) (FIG. 17B).

The pin (1705) when located in the channel (1704) exerts a positive compressing force on the rubber tube (1703) which closes the switch (1701). The frame continues to urge the pin toward the rubber tubing to actuate the switch (1701) into a closed condition (FIG. 17B). The switch (1701) now electrically connects the battery (not shown) to the controller to permit the dialysis device to be used by a patient. The fractured frame (1706) can no longer hold the pin (1705) rigidly upright for the pin (1705) to get inserted into the channel (1704) on the controller (1702) again.

Applications

It is an advantage of the device that as the flow path is fluidly sealed from the controller the sterility of the device can be maintained by daily disposal of disposable housing.

It is a further advantage of the dialysis device that a single connector between the disposable housing and controller is required, thus reducing the complexity of setting the device up for operation.

It is a further advantage that the size of the dialysis device according to the disclosure can be significantly reduced relative to other dialysis devices.

It is a further advantage that the device according to the disclosure is energy efficient.

It is an advantage of the device according to the disclosure that as the fluid displacement means is integrally formed with a wall of the storage chamber this permits the pumping mechanism of the dialysis device to be shared by the storage chamber thereby permitting a reduction in the size of the disposable housing. This is further advantageous as it permits the construction of a more portable and unobtrusive device to be used by a patient.

It is a further advantage that the connector between the disposable housing and the controller is fluidly sealed to prevent biological or chemical contamination of the device. It is an advantage of the device that, as the flow path is fluidly sealed from the controller, the risk of biological and/or chemical contamination of the dialysate by the controller is significantly reduced.

It is a further advantage of the device that as only one pump and only one interface connector is required this reduces the requirement for additional pumps and connections and thus results in a significant reduction in the size of the dialysis device relative to known dialysis devices.

It is a further advantage of the device of the disclosure that as only one pump is required to activate a storage chamber, an additive dispensing means and a gas vent means, this further permits miniaturization of the device and enhances portability and energy efficiency.

It is a further advantage that as only one pump is required to activate the storage chamber, the additive dispensing means and the gas vent means, there is a significant reduction in the complexity of the device which results in a decrease in manufacturing costs relative to known dialysis devices.

It is a further advantage of the device that the pressure sensor can also be used to measure a patient's intraperitoneal pressure, without additional pressure sensors.

Further embodiments of the present invention seek to provide a biocompatible and remote ammonia sensing system for peritoneal dialysis and haemodialysis. The sensing system can advantageously monitor a dialysate's ammonium level continuously in a safe manner, while overcoming the challenges of transporting a limited amount of ammonia gas to the ammonia sensing system. The sensing system is capable of monitoring the regenerated dialysate ammonium concentration from a remote distance, so as to function as a safety mechanism for a dialysis device. The sensing system according to example embodiments is especially suitable for miniaturized portable and wearable dialysis devices.

The inventors have recognized that miniaturized portable and wearable peritoneal dialysis devices require some specific application conditions such as: (i) keeping the ammonia sensing part away from the dialysate line to maintain the dialysate's sterility, (ii) keeping the ammonia sensing components away from the hydrophobic membrane to facilitate sorbent exchange, and ease of designing and assembling the controller and disposable dialysis housing, and (iii) making the dialysis device as portable and wearable as possible.

However, providing the above-mentioned specific application conditions pose several challenges. First, a limited amount of ammonia gas is generated at the hydrophobic barrier when the regenerated dialysate reaches its safe margin ammonium level. Second, delivering the limited amount of ammonia gas to the ammonia sensing system (which may be in a remote position) and detecting its presence can be difficult.

To transport a limited amount of ammonia gas to the ammonia sensing system, the gas connection conduits have to be ammonia gas compatible, which means the materials should not react with or adsorb ammonia gas nor release any ammonia gas or any similar chemicals.

To facilitate transportation of the limited amount of ammonia gas, gas transportation at the interface between the hydrophobic barrier and the ammonia detector has to be controlled. Additional means, including but not limited to introducing extra driving forces to deliver gas to the ammonia detector, can enhance the gas transport efficiency. This can increase the sensitivity of the remote ammonia sensing system.

Figure 18:
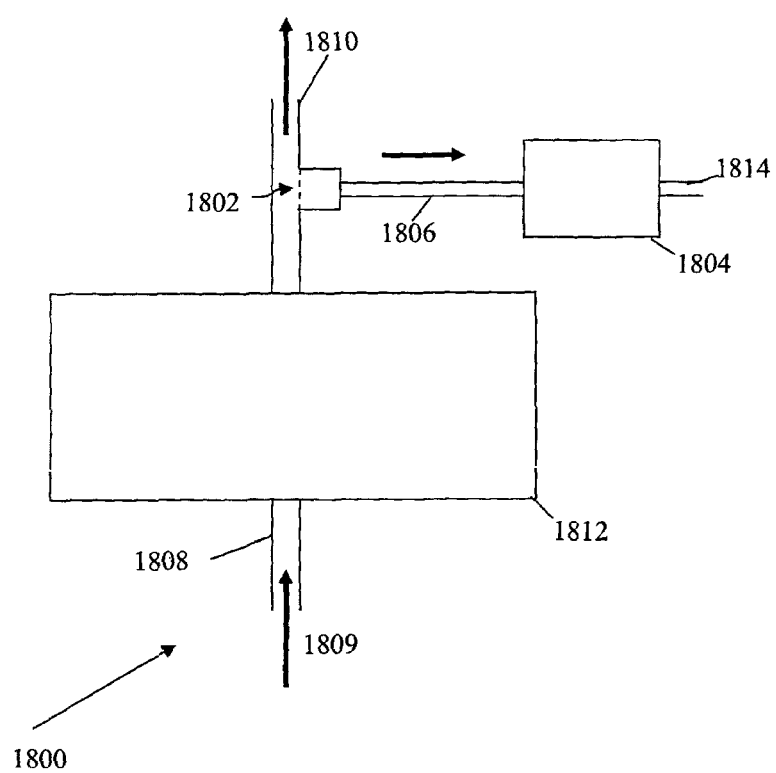
FIG. 18 is a schematic of an ammonia sensing system according to an embodiment of the invention.

FIG. 18 is a schematic of a sensing system 1800, according to an embodiment of the invention. The sensing system 1800 may include a gas "generator" 1802, a detector capable of detecting the generated gas 1804, an interface (e.g. a gas conduit or channel) 1806 between the gas generator 1802 and the detector 1804, and an electrical system including an appropriate set of firmware (not shown). In one embodiment, the sensing system 1800 is designed to sense ammonia gas. In this embodiment, the gas generator 1802 is an ammonia gas generator, and the detector 1804 is an ammonia/ammonium detector.

While the sensing system 1800 described above, and the various alternate embodiments of sensing systems described below are described in terms of ammonia detection, it is understood that other types of gasses may also be detected using the sensing systems described. By way of example and not limitation, the systems may be configured to detect volatile organic compounds (VOC) such as acetone or other biomarkers used for the detection of medical conditions, $CO_2$, $O_2$, $SO_2$, HCN, $NO_x$, etc. As discussed below, A dialysate flows into a liquid line 1808 at point 1809 and is passed through a sorbent cartridge comprising toxin removers 1812. The dialysate flows out after toxin removal at point 1810. The ammonia gas generator 1802 is in direct contact with the dialysate liquid flow coming from the toxin remover 1812.

The ammonia gas generator 1802 is the part where ammonia gas ($NH_3$) crosses a hydrophobic barrier, such as, but not limited to a hydrophobic membrane, a hollow fiber, etc, and enters the gas phase. Ammonia ($NH_3$) is in a pH dependent equilibrium with ammonium ($NH_4^+$) the dialysate. The ammonia gas generator 1802 is disposed at a point that is distal the ammonia detector 1804. The terms "ammonia" and "ammonium" may be used interchangeably in the following description, e.g. "ammonia/ammonium detector". In an example embodiment, the ammonium ($NH_4^+$) in the dialysate equilibrates to ammonia gas ($NH_3$). Although the "detector" is configured to detect ammonia gas, the concentration of $NH_4^+$ in the dialysate is proportional to the $NH_3$ gas generated. Thus, the "detector" can also be thought of as an ammonium detector. Accordingly, in the description, the two terms are to be taken as substantially equivalent.

In an embodiment, the ammonia gas generator 1802 may be a hydrophobic barrier. The hydrophobic barrier is in direct contact with the regenerated dialysate liquid flow. When there is ammonium present in the dialysate, the ammonium can equilibrate on the hydrophobic degasser barrier to generate ammonia gas. In one example embodiment, the hydrophobic barrier is a degasser membrane or degasser fabric/resin. In another embodiment, the hydrophobic barrier is a bacteria filter.

In an embodiment, the ammonia detector 1804 is capable of detecting the presence of ammonia gas in the ammonia gas generator 1802 of the hydrophobic barrier, which reflects the ammonium concentration in the regenerated dialysate on the other side of the hydrophobic barrier (at the liquid phase side of the hydrophobic barrier).

Various types of ammonia sensors may be used, including chemical sensors (e.g. chemical sensitive materials and matrix, pH sensitive colorimetric materials, etc.), electrical sensors (e.g. semiconductor based sensors, nano-particles, nano-wires and carbon nano-tubes, graphene sensors, etc.), biological sensors and their combinations and/or derivatives thereof. The terms "sensor" and "detector" may be used interchangeably in the description and are to be taken as substantially equivalent.

In an embodiment, the interface 1806 is a channel configured to allow fluid communication of the ammonia gas from the ammonia gas generator 1802 (at the gas phase side of the hydrophobic barrier) to the ammonia gas detector 1804 which is at a remote position. Materials used for the channel are preferably neutral or basic (i.e. ammonia-gas-compatible) and non-porous. Ammonia-gas-compatible materials neither adsorb nor release any ammonia gas or other similar chemicals. Non-porosity of the interface material advantageously minimizes unnecessary physical adsorption of the limited amount of ammonia gas. Suitable materials for the channel include, but are not limited to: metals, polytetrafluoroethylene (PTFE) ("Teflon"), polyvinyl chloride (PVC), acrylonitrile butadiene styrene (ABS), polyethylene (PE), and polypropylene (PP).

In another embodiment, sensitivity of the ammonia sensing system can be enhanced by optimizing the dimensions (e.g. length, thickness, etc.) of the gas channel. In one example embodiment, the channel is about 1 cm to about 50 cm in length.

In an embodiment, transportation of the ammonia gas to the ammonia gas detector may be enhanced by reducing liquid condensation within the interface. Since ammonia gas can be easily dissolved in a neutral aqueous liquid, a reduction of liquid condensation in the interface channel advantageously enhances ammonia gas transfer.

In an example embodiment, to enhance transportation of the ammonia gas, a heat isolation barrier may be used to reduce the heat loss and to keep the system temperature as constant as possible so as to minimize condensation. By way of example and not limitation, the heat isolation barrier may be a carrier bag having thermal isolation padding for storing the wearable dialysis device. In yet another embodiment, introduction of suitable ammonia-gas-compatible water absorbers within the gas channel advantageously absorb any potential condensation droplets. Suitable water adsorbers include, but are not limited to: alkaline or neutral materials, e.g. soda lime, cellulose and its derivatives based polymers, etc.

In a further embodiment, an ammonia-gas-compatible gas adsorber may be used within the channel to minimize interference and to enhance the sensitivity of the ammonia sensing system. Suitable adsorbers include, but are not limited to: alkaline or neutral materials, e.g. soda lime, cellulose and its derivatives based polymers, etc.

Ammonia gas that has passed beyond the ammonia detector 1804 may be exhausted at point 1814 using suitable means known to persons skilled in the art.

In an example embodiment, the remote ammonia sensing system comprises a delivery mechanism/medium capable of transporting the ammonia gas from the point that is distal the detector to the detector. In other words, the medium facilitates transportation of the generated ammonia gas from the hydrophobic barrier along the interface to the ammonia sensor/detector. The medium can be chosen from a list of gases, and electrical or magnetic field.

In one example embodiment, the gas is circulated around the gas phase side of the hydrophobic barrier to facilitate transportation of the ammonia gas from an immediate position to a remote position of the gas phase side of the hydrophobic barrier. The circulated gas delivers the ammonia gas to the ammonia detector. In this embodiment, an extra pump may be used to provide an extra driving force.

Figure 19:
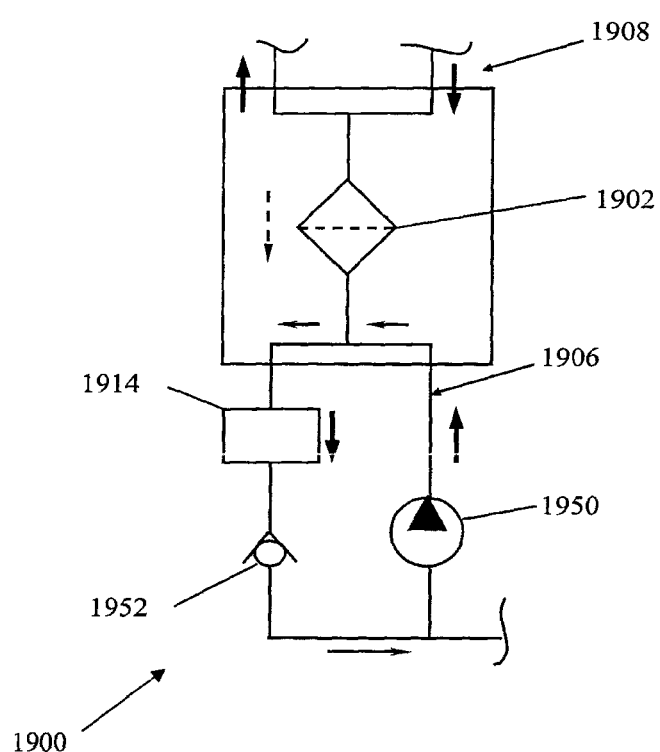
FIG. 19 is a schematic of another ammonia sensing system according to an embodiment of the invention.

FIG. 19 is a schematic of an ammonia sensing system 1900 using gas circulation, according to an embodiment of the invention. The system 1900 includes a pump 1950 capable of providing an extra driving force. A dialysate flow path 1908 is separated from a gas flow path 1906 by an ammonia gas generator 1902. An ammonia detector 1914, check valve 1952, and the pump 1950 are operably connected to the gas flow path 1906. The pump 1950 provides a driving force to circulate the ammonia gas and other degassed gas mixture around the gas flow path 1906. A one-way pump may be used, together with the check valve 1952 to create a unidirectional flow of gas around the gas flow path 1906. The circulation configuration also has an advantage over the back and forth pump configuration in that only the delivery medium with highest concentration of ammonia gas from the generator is pushed to the detector. This configuration may thus provide a higher sensitivity for the system.

In another embodiment, the degassed gas is moved back and forth within the gas loop to deliver the ammonia gas to the remote position of ammonia detector. In this embodiment, an extra two-way pump may be used to provide the driving force.

Figure 20:
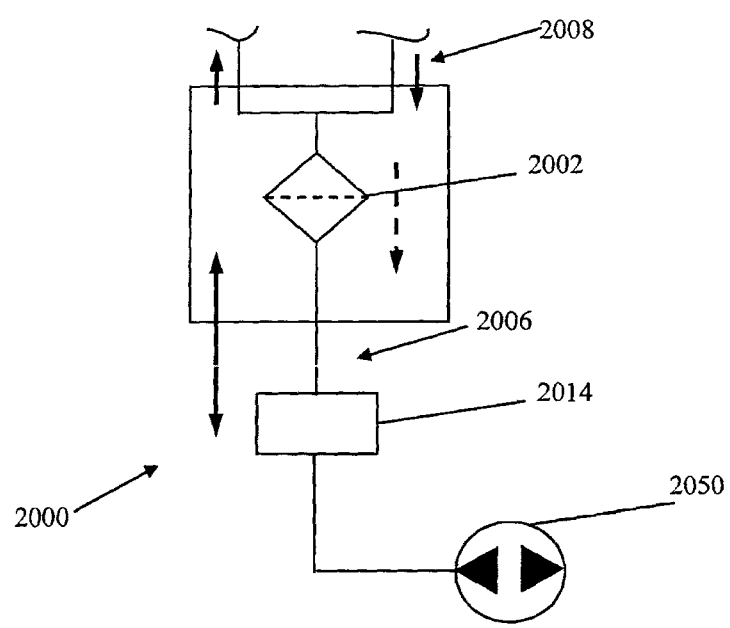
FIG. 20 is a schematic of a further ammonia sensing system according to an embodiment of the invention.

FIG. 20 is a schematic of an ammonia sensing system 2000 with providing reciprocating (back and forth movement) of the gas, according to an embodiment of the invention. The system 2000 includes a pump 2050 capable of providing an extra driving force. A dialysate flow path 2008 is separated from a gas flow path 2006 by an ammonia gas generator 2002. An ammonia detector 2014, and the pump 2050 are operably connected to the gas flow path 2006. The pump 2050 may be a two-way pump to move the gas back and forth within the gas flow path 2006. In this embodiment, an advantage that the back and forth motion of the gas provides over the circulation type pump is that, when the gas is pushed over the hydrophobic barrier, it helps to ameliorate any potential micro-liquid-droplets blocking the barrier. This configuration produces less condensation in experimental configurations compared to the circulation configuration. In this embodiment, the back and forth motion of the gas has one advantage over the circulation type pump. When the gas is pushed over the hydrophobic barrier, it helps to ameliorate any potential micro-liquid-droplets blocking the barrier. This configuration produces less condensation in experimental configurations compared to the circulation configuration.

In yet another embodiment, an external gas may be used as the delivery/carrier gas to deliver the ammonia gas to the remote position of the ammonia detector. In this embodiment, the external gas may be introduced to the gas loop via the main pump 2150 (see FIG. 20). This is more clearly illustrated in FIG. 25. During the inflow phase of the whole system, the system firmware controls the motion of the valve 2506. Since the main system is under positive pressure, a controlled portion of gas is released into the gas interface via valve 2504, and subsequently reaches the generator 2562 (hydrophobic barrier). Suitable external gases include, but are not limited to: air or nitrogen.

Four example configurations of embodiments of the system are illustrated in FIGS. 21(a) to (d). All four configurations comprise a dialysate flow path 2108 being separated from a gas flow path 2106 by an ammonia gas generator 2102. An ammonia detector 2114, check valves 1952a/b, a valve 2154, and a pump 2150 are operably connected to the gas flow path 2106. In some embodiments, the valve 2154 may be a switch concept valve coupling with or without an orifice, a solenoid valve, or other types of valves know to those of skill in the art.

Figure 21A:
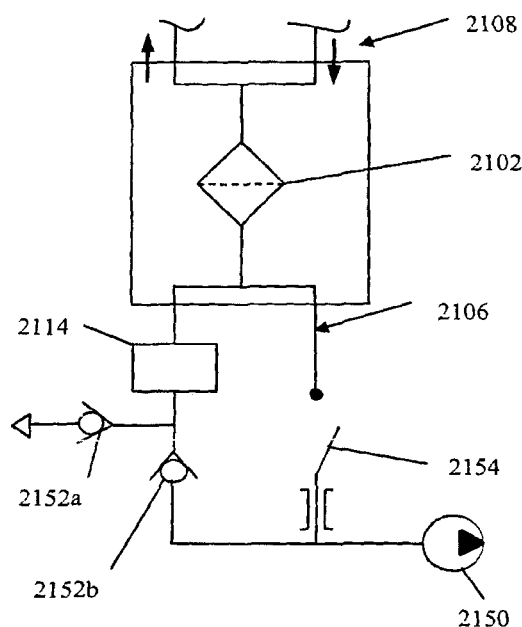
FIGS. 21a-21d provide schematics of four example configurations of embodiments of the ammonia sensing system.
Figure 21B:
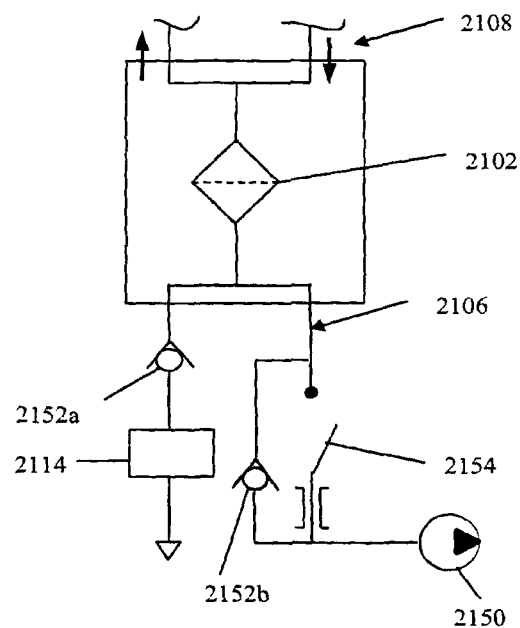
Figure 21C:
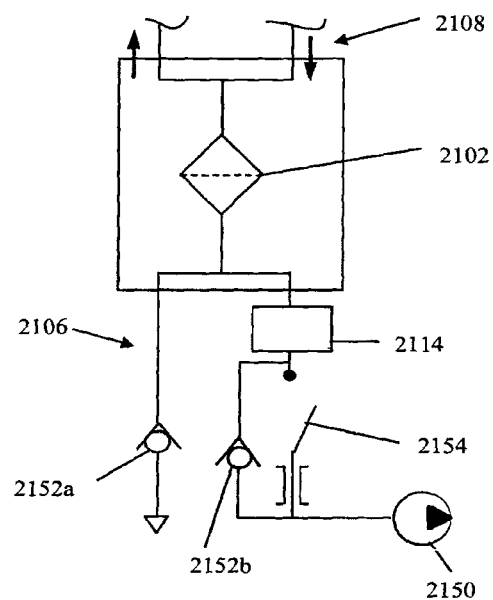
Figure 21D:
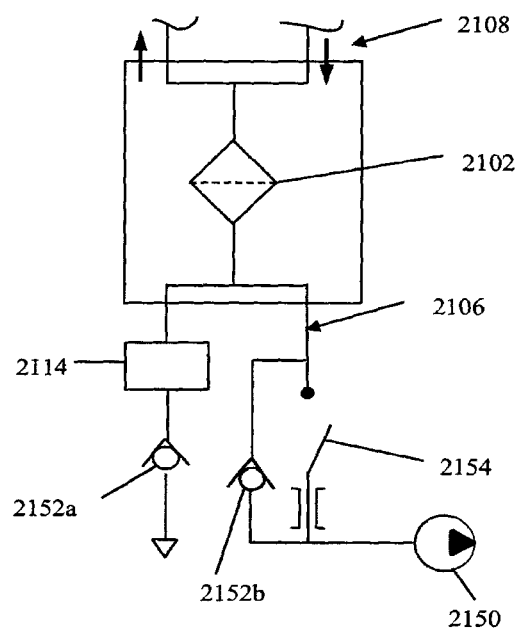
Figure 22A:
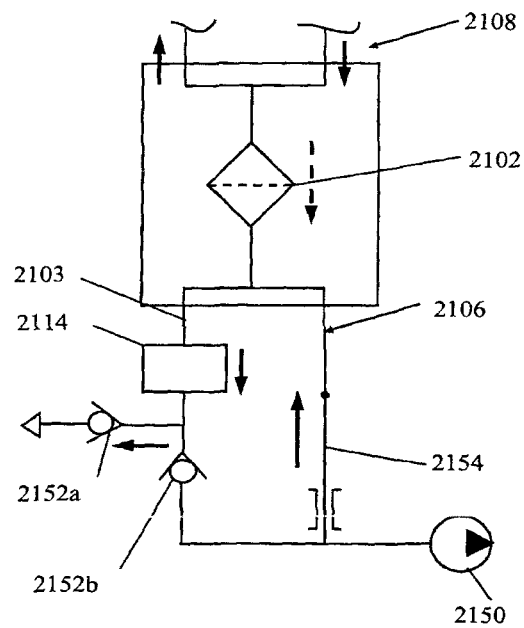
Figure 22B:
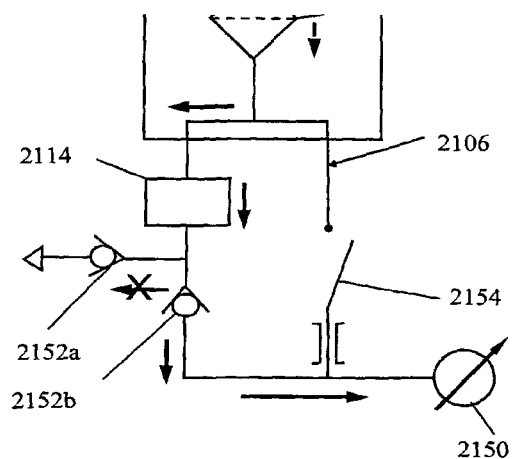

In more detail, the gas connection pattern of the first configuration (i.e. FIG. 21(a)) was optimized to illustrate the dialysate in-flow and dialysate out-flow phases as shown in FIGS. 22(a) and (b) respectively. During the in-flow phase, the valve 2154 is connected. The gas flows through the ammonia sensor 2114 and check valve 2152a; and ammonia gas is exhausted from the gas flow path 2106. During the out flow phase, the valve 2154 is disconnected. The gas flows through the ammonia sensor 2114 and check valve 2152b; and exits the gas flow path 2106 via valve 2150 back to the dialysis device.

In more detail, the gas connection pattern of the first configuration (i.e. FIG. 21(a)) was optimized to illustrate the dialysate in-flow and dialysate out-flow phases as shown in FIGS. 22(a) and (b) respectively. In FIG. 22a, during the in-flow phase, the main operational system is under positive pressure. The firmware connects valve 2154. The gas flows from pump 2150 to the gas channel 2106. The transport medium reaches the ammonia gas generator 2102 first, then through the gas interface 2103 (which is between the generator 2102 and the detector 2114) to the ammonia sensor 2114.

During the out flow phase, the main system is under negative pressure and the firmware disconnects valve 2154. No external gas goes into the gas channel. The gas channel is evacuated by the main pump 2150. The degassed gas passes the gas interface and reach ammonia/ammonium detector. Due to the fact that the gas channel pressure is lower than the external pressure of the system, the gas further moves to the valve 2152b rather than valve 2152a. The gas flows through the valve 2152b to the main system exhaust (FIG. 25 2158) via the main pump 2150.

A combination of the above mechanisms may be used to facilitate transportation of the ammonia gas from the point that is distal the detector to the detector. For example, a carrier gas comprising nitrogen may be used in conjunction with a two-way pump. In other applications, an alternate carrier gas including, but not limited to air, and/or other gases may be used.

When using a delivery/carrier gas, either a continuous or intermittent gas pattern can be used. The amount of delivery gas within the gas conduit is preferably optimized. Too little delivery gas may not produce sufficient driving forces to transport the ammonia gas to the ammonia detector. On the other hand, too much delivery gas flow may dilute the limited amount of ammonia gas, possibly resulting in the ammonia gas concentration falling out of the detection limit of the ammonia detector. By optimizing the delivery gas flow, the ammonia gas is transported to the ammonia detector within the desired time. In one example embodiment, the gas flow range is about 2-50 ml/min, and/or 5-200 ml/stroke. An optimized result in the embodiment is about 5-25 ml/min and/or 30-70 ml/stroke.

The continuous carrier gas pattern, after proper optimization, is theoretically more efficient in gas delivery. However, it consumes relatively more power and may need an extra pump to drive the carrier gas.

The intermittent carrier gas pattern requires less power, and can use the main gas pump 2512 of the dialysis controller device 2500 (see FIG. 25) to release the required amount of carrier gas into the system at the required time points.

In an embodiment, an electronic control means and processor (i.e. the electrical system and firmware) controls the driving force for the transportation of ammonia gas to a remote position and to function as an automated controller. A suitable set of firmware may include the timing control for opening and closing of the valve in the gas flow path so as to deliver the ammonia gas from the gas generator to the ammonia detector, synchronizing the ammonia sensor read-back with the valve timing control, determination of the gradient and/or comparison with a pre-determined threshold for the ammonia signal, and activation of the alarm system.

Figure 23:
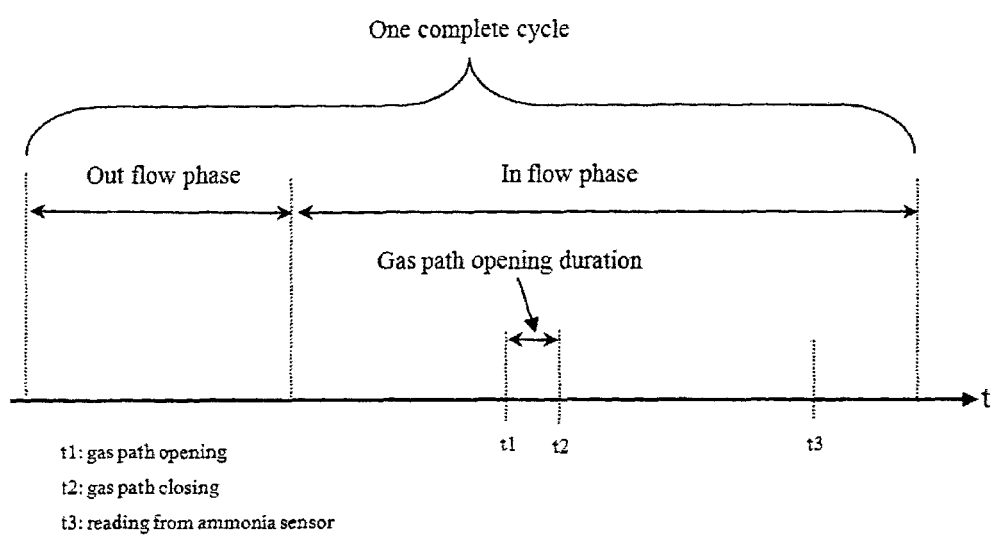

FIG. 23 shows one timing diagram for a control method implemented for the first configuration (i.e. FIG. 21(a)). In every cycle, there are two distinct phases—an out flow phase and an in flow phase. During the in flow phase, the gas path is opened from time t1 to t2. At time t3, the reading from the ammonia sensor is obtained. The control method is installed in the controller firmware. The control is implemented during the inflow phase when the pressure difference between the internal cartridge and the degasser channel is more significant and stable than the outflow phase. A high pressure gradient is more favorable for the penetration of ammonia gas through the membrane into the interface of the gas generator and the ammonia gas detector.

In some embodiments a pressure gradient of 10-760 mmHg is possible. A pressure gradient of 50-200 mmHg may be preferred for some embodiments. In other embodiments, the t1-t2 interval may be 0-30 s. In a preferred embodiment 1-10 s may be used. In other embodiments, t3 can be t2+(1 second or more) to the end of the cycle. In a preferred embodiment, t3 is t2+(20-100 seconds).

Two different methods may be used to determine the ammonia signal level. The first method is to directly obtain the readings from the ammonia detector after the settling time of the ammonia signal. The second method is to use the minimum or maximum value of the ammonia signal readings which are obtained at a predetermined rate (e.g. 1 Hz) during the inflow phase.

If no ammonium or a safe level of ammonium is present in the regenerated dialysate (i.e. the sorbent cartridge functions well and is yet to be exhausted), the equilibrium of ammonium and ammonia gas over the hydrophobic barrier hardly generates any ammonia gas on the gas phase of the hydrophobic membrane. When the delivery gas mechanism is triggered, the degassed gas and the inner delivery gas are transported to the ammonia detector. The ammonia detector does not react to this gas mixture and the processed sensor signal remains within the safe range. The gradient of the ammonia signal is calculated from the readings of two consecutive flow cycles except for the first cycle where no gradient of the signal is available. No high concentration ammonia gas or system malfunction alarm is triggered.

If the ammonium level in the regenerated dialysate approaches the safety margin (i.e. the sorbent cartridge malfunctions or is about to be exhausted), the ammonium/ammonia equilibrium over the hydrophobic barrier causes ammonia gas to be present in the gas phase over the hydrophobic barrier. When the delivery gas mechanism is triggered, the delivery gas transports the ammonia gas along the gas channel to the ammonia detector. The ammonia detector reacts with the ammonia gas and generates an alarm signal. The gradient of the ammonia signal is calculated from the readings of two consecutive flow cycles. The alarm may be configured to activate when the ammonia signal reading exceeds a pre-determined threshold and the signal gradient is positive (i.e. indicating an increase in the amount of ammonium/ammonia in the system).

Figure 24A:
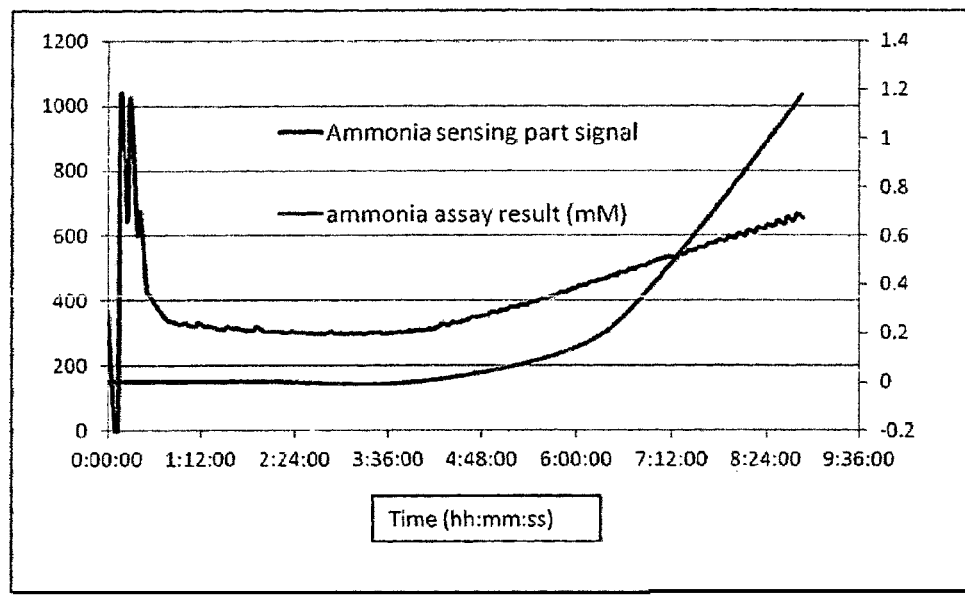
FIGS. 24(a) and (b) are graphs showing the results obtained from one example embodiment of the present invention using an electrical ammonia detector.
Figure 24B:
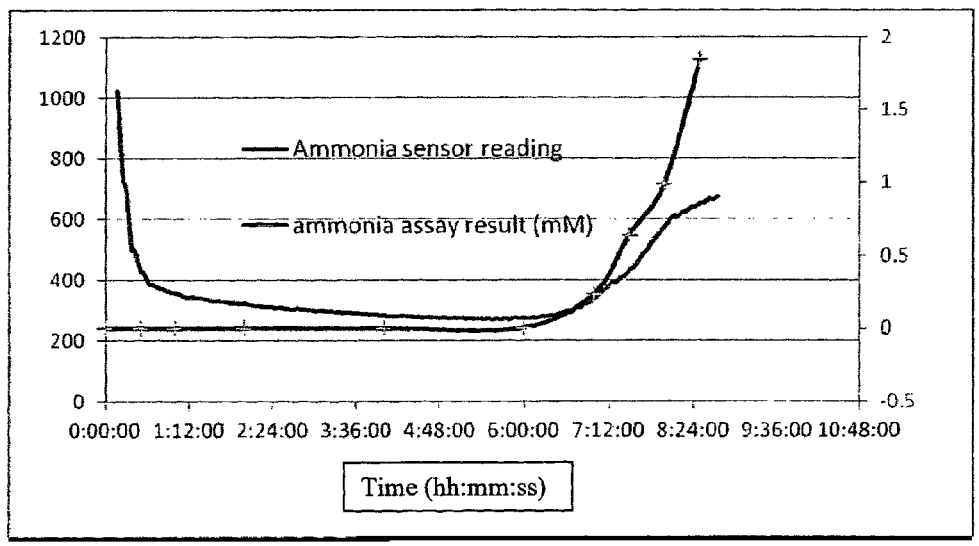

FIGS. 24(a) and (b) are graphs showing the results obtained from one example embodiment of the present invention using an electrical ammonia detector. In FIG. 24(a), as the level of ammonia in the system rises over time (as reflected by the increase in concentration of ammonia (in mM) from the ammonia assay result), the signal of the ammonia sensing part of the ammonia detector increases correspondingly. In an embodiment, an alarm can be configured to trigger when a predetermined signal level is reached. In FIG. 24(b), as the level of ammonia in the system rises over time (as reflected by the increase in concentration of ammonia (in mM) from the ammonia assay result), the readings obtained from the ammonia sensor/detector increase correspondingly. With respect to both FIGS. 24(a) and 24(b), the right y-axis reflects the actual ammonia concentration in mM, while, the left y-axis is a value that is directly proportional and related to the voltage of the analogue signal from the sensor.

Figure 25:
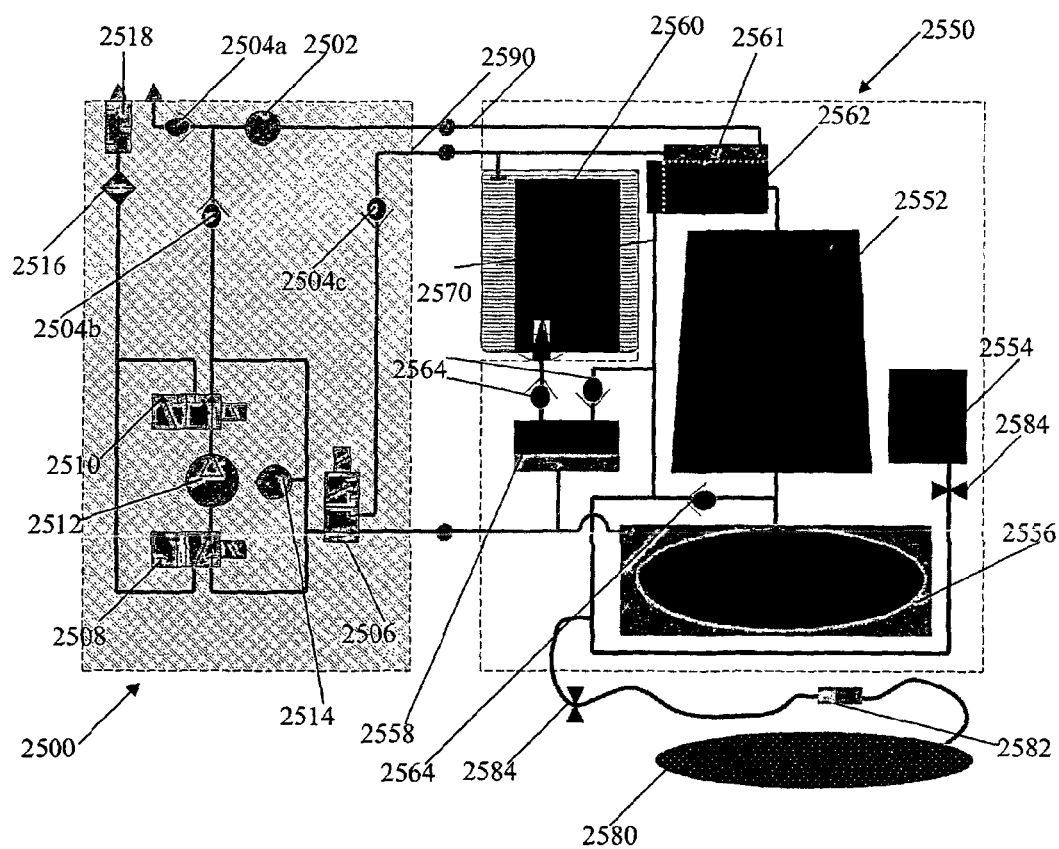
FIG. 25 is a schematic of a controller system for an ammonia sensing system according to an embodiment of the invention, in fluid communication with a disposable sorbent cartridge of a dialysis device.

FIG. 25 is a schematic of a controller system 2500 according to an embodiment of the invention, in fluid communication with a disposable sorbent cartridge 2550 of a dialysis device. The disposable sorbent cartridge 2550 comprises a toxin adsorber 2552, a UF bag 2554, storage module/pneumatic pump 2556, infusate pump 2558, infusate reservoir 2560, degasser/sterile filter 2562, and check valves 2564. The disposable sorbent cartridge 2550 is connected to a patient's peritoneal cavity 2580 via connector 2582. Pinch clamps 2584 may be used on appropriate fluid lines. The workings and/or connections of the components in the disposable sorbent cartridge 2550 are not relevant for the current purpose of understanding the connection of the disposable sorbent cartridge 2550 to the ammonia sensing system 2500 according to an embodiment of the invention.

The controller system 2500 comprises an ammonia detector 2502, check valves 2504, valves 2506/2508/2510, a pump 2512, a pressure sensor 2514, a safety screen 2516, and an exhaust means 2518. In one embodiment, the safety screen 2516 may be, by way of example and not limitation, a 5 µm metal screen.

In this embodiment, the system 2500 is a controller system the system 2500 includes the ammonia sensing system as described above, including an ammonia gas generator 2562 a gas interface 2590, an ammonia detector 2502, check valves 2504a-c, and one more valves 2506, which is connected to 2504c. The ammonia sensing system is part of the main controller system plus a part of a disposable cartridge which can be used in the portable dialysis system.

After passing through the degasser 2562 in the disposable sorbent cartridge 2550, the dialysate passes through the dialysate line 2570 and is re-constituted with the infusate concentrate in 2560 by the infusate pump 2558, then returned to the patient via the valve 2564, pinch clamp 2584 and connector 2582. The ammonia gas equilibrated over the generator (hydrophobic barrier 2561) is transported to the ammonia detector 2502 via the interface/channel 2590. After passing through the ammonia detector 2502, the gas mixture is exhausted through check valve 2504a during the inflow phase, or is exhausted through check valve 2504b, 2510, 2512, 2508, 2516 and 2518 during the outflow phase.

Embodiments of the present invention provide several advantages. The ammonia gas detector is separated from the ammonia gas generator and located at a remote position. In other words, the ammonia gas detector is spatially isolated from the liquid line, advantageously maintaining the dialysate's sterility. Additionally, the system provides for ease of assembly in disposable or partially disposable devices.

Furthermore, the ammonia sensing system with integrated degassers, sterile filters, and/or other functional hydrophobic barriers (acting as the ammonia gas generator), and pump system allows a compact system design.

The integrated gas transport mechanism/medium between the ammonia gas generator and ammonia gas detector advantageously improves the sensitivity of the sensing system, such that a limited amount of ammonia can be detected.

Furthermore, using appropriate controller firmware with suitable detection algorithms, the ammonia sensing system can be fully automated.

The biocompatible and remote ammonia sensing system according to embodiments of the invention as described above may be incorporated into a dialysis device. The dialysis device may be a peritoneal dialysis device or a hemodialysis device.

An embodiment of the present invention also relates to a method of detecting ammonium in a dialysate, comprising the steps of: providing a detector capable of detecting ammonia gas; and providing a channel configured to allow fluid communication of the ammonia gas; wherein the channel is disposed between the detector and a point distal the detector; the point being where ammonium in the dialysate equilibrates to form ammonia gas.

In yet another embodiment of the invention, the biocompatible and remote ammonia sensing system according to embodiments of the invention as described above may be modified to detect other fluids (e.g. other gases present in a dialysate). By way of example and not limitation, the systems may be configured to detect volatile organic compounds (VOC) including, but not limited to acetone, $CO_2$, $O_2$, $SO_2$, HCN, $NO_R$, etc.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A sensing system for detecting a substance in a dialysate, comprising:
    a hydrophobic barrier capable of allowing the substance in the dialysate to equilibrate through the barrier to a gas;
    a detector capable of detecting the gas;
    an interface disposed between the hydrophobic barrier and the detector and configured to allow fluid communication of the gas between the hydrophobic barrier and the detector; and
    one or more delivery mechanisms capable of transporting the gas from the hydrophobic barrier through the interface to the detector and wherein the one or more delivery mechanisms allows the gas to move either back and forth within the interface, or forth to the detector.

2. The sensing system as claimed in claim 1, wherein the one or more delivery mechanisms provides a driving force capable of transporting the gas.

3. The sensing system as claimed in claim 2, wherein the driving force circulates the gas within the interface.

4. The sensing system as claimed in claim 2, further comprising an electronic controller configured to control the driving force.

5. The sensing system as claimed in claim 1, wherein the one or more delivery mechanisms comprise a carrier gas.

6. The sensing system as claimed in claim 1, wherein the interface is about 1 cm to 50 cm in length.

7. The sensing system as claimed in claim 1, wherein the substance is ammonium and the gas is ammonia gas.

8. The sensing system as claimed in claim 7, wherein the hydrophobic barrier is capable of separating the ammonium in the dialysate from the ammonia gas in the interface.

9. The sensing system as claimed in claim 1, wherein the substance is a volatile organic compound.

10. The sensing system as claimed in claim 1, wherein the hydrophobic barrier comprises a degasser barrier.

11. The sensing system as claimed in claim 1, wherein the hydrophobic barrier comprises a bacteria filter.

12. The sensing system as claimed in claim 1, wherein the hydrophobic barrier is in direct contact with the dialysate.

13. The sensing system as claimed in claim 1, wherein the interface comprises one or more ammonia gas compatible materials.

14. The sensing system as claimed in claim 1, wherein the interface comprises a non-porous material.

15. The sensing system as claimed in claim 1, wherein the interface comprises an ammonia-gas-compatible water absorber within the interface.

16. The sensing system as claimed in claim 1, further comprising an electronic processor electrically connected to the detector, the electronic processor configured to obtain readings from the detector, process the readings and/or trigger an alarm when the readings exceed a predetermined threshold.

17. A dialysis device comprising: the sensing system as claimed in claim 1; and a sorbent cartridge, wherein the detector is an ammonia detector that is capable of detecting ammonia gas, wherein the gradient of the amount of detected ammonia gas provides an indication of the exhaustion of the sorbent cartridge.

18. The dialysis device as claimed in claim 17, wherein the dialysis device comprises a peritoneal dialysis device.

19. The dialysis device as claimed in claim 17, wherein the dialysis device comprises a hemodialysis device.

* * * * *